United States Patent [19]

Packett

[11] Patent Number: 5,312,996
[45] Date of Patent: May 17, 1994

[54] HYDROFORMYLATION PROCESS FOR PRODUCING 1,6-HEXANEDIALS

[75] Inventor: Diane L. Packett, South Charleston, W. Va.

[73] Assignee: Union Carbide Chemicals & Plastics Technology Corporation, Danbury, Conn.

[21] Appl. No.: 62,475

[22] Filed: May 20, 1993

Related U.S. Application Data

[63] Continuation-in-part of Ser. No. 905,415, Jun. 29, 1992, abandoned.

[51] Int. Cl.$^5$ .............................................. C07C 45/50
[52] U.S. Cl. ................................... 568/454; 568/451
[58] Field of Search ................................ 568/451, 454

[56] References Cited

U.S. PATENT DOCUMENTS

| | | | |
|---|---|---|---|
| 3,527,809 | 9/1970 | Pruett et al. | 568/454 |
| 3,947,503 | 3/1975 | Kummer | 260/635 |
| 4,148,830 | 4/1979 | Pruett et al. | 568/454 |
| 4,247,486 | 1/1981 | Brewester et al. | 568/454 |
| 4,248,802 | 6/1981 | Kuntz | 568/455 |
| 4,507,508 | 5/1983 | Hayden et al. | 568/487 |
| 4,599,206 | 12/1984 | Billig et al. | 558/85 |
| 4,742,178 | 11/1986 | Nelson et al. | 568/454 |
| 4,769,498 | 2/1987 | Billig et al. | 568/454 |
| 4,808,756 | 10/1987 | Yasso et al. | 568/454 |

OTHER PUBLICATIONS

Tetrahedron Letters, 1969, 32,2721–2723, "Dialdehydes by Hydroformylation of Conjugated Dienes".
Chemike–Zeitung, 1975, 99, 452–458, "Hydroformylation of Conjugated Dienes. II Cobalt Carbonyl and Rhodium Carbonyl Catalyst Systems in Hydroformylation of 1,3-Dienes".
Chemike–Zeitung, 1975, 99,485–492, "Hydroformylation of Conjugated Dienes".
Journal of Organometallic Chemistry, 1980, 184, C-1-7–C19, "Optically Active Aldehydes via Hydroformylation of 1,3-Dienes with Chiral Disphosphinerhodium Complexes".
Journal of Molecular Catalysis, 1985, 31, 345-353, "The Hydroformylation of Butadiene Catalyzed by Rhodium-Diphosphine Complexes".
J. Falbe "New Syntheses with Carbon Monoxide" Springer–Verg NY 1980.
Symp. Rhodium Homogeneous Catalysis, 1978, 87–93, "Diols by Hydroformylation of Conjugated Dienes".
Journal of Molecular Catalysis, 1980, 8, 329–337, "The Hydroformylation of Conjugated Dienes. VI Tertiary Aryl- and Alkylphosphines and Secondary Aryl- and Alkylphosphines as Ligands in the Rhodium Catalyzed Hydroformylation Reaction of Conjugated Dienes to Dialdehydes".
III. "Reaction Products of a Hydroformylation of Conjugated Dienes with Rhodium Carbonyl/tert-Phosphine Catalyst Systems".
Journal of Molecular Catalysis, 1977, 2,211–218, "The Hydroformylation of Conjugated Dienes V. Aliphatic Tertiary Phosphines and P-Substituted Phospholanes as Co-Catalysts of the Rhodium-Catalyzed Hydroformylation of 1,3-Dienes".

*Primary Examiner*—Werren B. Lone
*Attorney, Agent, or Firm*—E. C. Trautlein

[57] ABSTRACT

This invention relates to a hydroformylation process for producing a 1,6-hexanedial which comprises reacting a butadiene with hydrogen and carbon monoxide in the presence of a catalytic amount of rhodium complexed with certain poly-phosphite ligands to achieve high conversions of the butadiene to the 1,6-hexanedial.

16 Claims, No Drawings

HYDROFORMYLATION PROCESS FOR PRODUCING 1,6-HEXANEDIALS

CROSS REFERENCE TO RELATED APPLICATION

This application is a continuation-in-part of U.S. patent application Ser. No. 07/905,415; filed Jun. 29, 1992, now abandoned.

FIELD OF THE INVENTION

This invention relates to the use of certain polyphosphite ligands in the rhodium-catalyzed hydroformylation of butadienes to produce 1,6-hexanedials. As used herein, the term "butadienes" denotes butadiene and substituted butadiene (e.g., isoprene and dimethylbutadiene) and the term "1,6-hexanedials" denotes 1,6-hexanedial (i.e., adipaldehyde) and substituted 1,6-hexanedial (e.g., 2-methyl-hexane-1,6-dial and 3,4-dimethyl-1,6-hexanedial).

BACKGROUND OF THE INVENTION

Adipaldehyde is a valuable intermediate which is useful, for example, in the production of e-caprolactone by the Tischenko reaction, in the production of adipic acid by oxidation and in the production of 1,6-hexanediol by hydrogenation. Adipic acid and 1,6-hexanediol are also produced from other intermediates (e.g., adipic acid is also produced from cyclohexanone by oxidation. Adipaldehyde itself is produced by circuitous routes such as by the ozonolysis of cyclohexane. The processes currently used to produce adipaldehyde, e-caprolactone, adipic acid and 1,6-hexanediol have various disadvantages. For example, the oxidation reactions may involve the use of nitric acid which can produce nitrous oxide which is an ozone scavenger and which, therefore, may contribute to the greenhouse effect. Moreover, starting materials currently used to produce adipaldehyde, adipic acid and 1,6-hexanediol are relatively expensive. Accordingly, it would be desirable to produce adipaldehyde from a relatively inexpensive starting material (e.g., butadiene) and by a process (e.g., hydroformylation) which does not have the disadvantages of prior art processes. However, prior art processes for producing adipaldehyde by the hydroformylation of butadiene have not been especially satisfactory. In particular, the selectivity to adipaldehyde in prior butadiene hydroformylation processes has been low. Such prior art hydroformylation processes are described below.

Various publications disclose the hydroformylation of butadiene with rhodium catalysts modified by secondary or tertiary, alkyl/aryl phosphines and phosphites to produce dialdehydes but the selectivity to adipaldehyde is less than 10% with most of the dialdehyde product being branched. The conditions used are typically rather severe such as pressures over 750 bar (i.e., pressures over 11,025 psi). Among such publications are: (1) Tetrahedron Letters, 1969, 32,2721–2723, "Dialdehydes by Hydroformylation of Conjugated Dienes"; (2) Chemike-Zeitung, 1975, 99, 452–458, "Hydroformylation of Conjugated Dienes. II Cobalt Carbonyl and Rhodium Carbonyl Catalyst Systems in Hydroformylation of 1,3-Dienes"; (3) Chemike-Zeitung, 1975, 99,485–492, "Hydroformylation of Conjugated Dienes. III. Reaction Products of a Hydroformylation of Conjugated Dienes with Rhodium Carbonyl/tert-Phosphine Catalyst Systems"; (4) Journal of Molecular Catalysis, 1977,2,211–218, "The Hydroformylation of Conjugated Dienes V. Aliphatic Tertiary Phosphines and P-Substituted Phospholanes as Co-Catalysts of the Rhodium-Catalyzed Hydroformylation of 1,3-Dienes"; and (5) Symp. Rhodium Homogeneous Catalysis, 1978, 87–93. "Diols by Hydroformylation of Conjugated Dienes"; and (6) Journal of Molecular Catalysis, 1980, 8, 329–337, "The Hydroformylation of Conjugated Dienes. VI Tertiary Aryl- and Arylalkylphosphines and Secondary Aryl- and Alkylphosphines as Ligands in the Rhodium Catalyzed Hydroformylation Reaction of Conjugated Dienes to Dialdehydes". Publication (5) above describes conducting the hydroformylation in methanol solvent to form aldehyde acetals but the selectivity to adipaldehyde acetal was still less than 10%.

Other publication describe the hydroformylation of butadiene by rhodium catalysts modified with bidentate (i.e., diphosphorus) phosphine (diphosphine) ligands. No mention of phosphite or bis-phosphite ligands is made in these publications and the major product in each case is a saturated monoaldehyde. These publications are: (a) Journal of Organometallic Chemistry, 1980, 184, C17–C19, "Optically Active Aldehydes via Hydroformylation of 1,3-Dienes with Chiral Diphosphinerhodium Complexes"; (b) European Patent 33/554 A2, "A Process For the Hydroformylation of Conjugated Dienes"; and (c) Journal of Molecular Catalysis, 1985, 31, 345–353, "The Hydroformylation of Butadiene Catalyzed by Rhodium-Diphosphine Complexes". Publication (b) above discloses the use of such catalysts to produce valeraldehyde and to minimize the production of dialdehydes. Publication (c) above discloses that butadiene complexes with rhodium thus blocking its activity in heptene-1 hydroformylation.

European patent application 309,056 discloses the hydroformylation of V-olefins or V,l-diolefins with rhodium catalysts modified by bis(phosphinoalkyl)ether ligands, $(R_2PCH_2CH_2)_2O$. No mention of phosphite or poly-phosphite ligands or of butadiene reactants is made in that patent application.

U.S. Pat. No. 4,507,508 discloses a process for the hydroformylation of butadiene and other conjugated diolefins using a rhodium catalyst modified by a tertiary phosphine or phosphite ligand in the presence of an alcohol and a strong acid. The phosphites have alkyl, aryl, aralkyl or alkaryl groups containing from 10 to 30 carbon atoms and the alcohols contain from 1 to 4 carbon atoms. No mention of bidentate phosphites (bis-phosphites) is made. All the Examples in this patent use triphenylphosphine as the ligand and there is no Example using a phosphite ligand. Selectivities to dialdehydes of up to 80% are achieved, but the nature of the dialdehydes, whether branched or linear, is not specified. Based on other publications showing the use of phosphine ligands (i.e., Chem. Zeit 1975 99 485; ibid. 1975 99 452; J Mol Cat 1980 329; ibid. 1977 2 211; and Tet Lett 1969 32 ibid 2721), the dialdehydes produced in U.S. Pat. No. 4,507,508 were probably branched.

U.S. Pat. No. 3,947,503 discloses a two-step process for the hydroformylation of butadiene. In the first step, butadiene is hydroformylated using a rhodium catalyst modified by a tertiary phosphine or phosphite in the presence of an alkanol or alkanediol to produced an acetal of 3-pentene-1-al. The hydroformylation in the first step is said to occur at 50–600 atmospheres pressure (700–9000 psi). In the second step, the acetal is hydroformylated using a cobalt catalyst modified by a tertiary phosphine to produce dialdehyde acetal. The use of a cobalt catalyst in the second step is stated in the patent to be crucial in order to obtain a linear dialdehyde acetal. The dialdehyde acetal is then hydrogenated to 1,6-hexanediol. Up to 50% isolated yields (based on butadiene) are reported. The patent contains only one Example and in it a phosphine ligand is used. Poly-phosphites are not mentioned in this patent.

U.S. Pat. No. 4,769,498 discloses poly-phosphites and their use as ligands in rhodium-catalyzed olefin hydroformylation. The olefins to be hydroformylated are broadly described in this patent as: "terminally or internally unsaturated and of straight chain, branched chain, or cyclic structure. Such olefins can contain from 2 to 20 carbon atoms and may contain one or more ethylenic unsaturated groups". The patent names several specific mono-olefin reactants and two specific non-conjugated diolefin reactants (i.e., 1,4-hexadiene and 1,7-octadiene). Conjugated diolefins such as butadiene, which often considered special cases in hydroformylation reactions (see Chem. Zeit. 1975 99, 452; ibid. 1975 99 485; and J. Falbe "New Syntheses with Carbon Monoxide" Springer-Verlag NY, 1980, Pages 103-105), are not specifically disclosed in this patent and no Examples showing the hydroformylation of any butadiene are included.

U.S. Pat. No. 4,599,206 discloses the use of diorgano phosphite ligands in the rhodium-catalyzed hydroformylation of olefins. The disclosure of olefins in this patent is similar to the disclosure of olefins in U.S. Pat. No. 4,769,498 discussed above. That is, there is no specific disclosure of the hydroformylation of any butadiene.

U.S. Pat. No. 4,742,178 discloses the low-pressure (15-800 psi) hydroformylation of dienes containing 6 to 10 carbon atoms with a catalyst consisting of rhodium and various chelating diphosphine ligands containing certain biphenyl bridging groups. Examples using other chelating diphosphines are included for comparison. The hydroformylation of 1,7-octadiene to produce 1,10-decanedialdehyde in high conversion and selectivity is disclosed in the Examples and 1,7-octadiene is the only diolefin used in the Examples of this patent. This patent illustrates the relative ease with which non-conjugated dienes can be converted to alkanedials by prior art processes. However, no mention is made of hydroformylation of any butadiene or of catalysts containing mono-phosphites or poly-phosphites.

U.S. Pat. No. 4,808,756 discloses the hydroformylation of V,l-diolefins containing from 6 to 10 carbon atoms or V,l-alkenals containing from 7 to 10 carbon atoms with a catalyst consisting of rhodium and a monodentate sulfonated or carboxylated phosphine in an aqueous solution of sulfolane and extraction of the reaction mixture with an alcohol or hydrocarbon. The Examples show the hydroformylation of 7-octene-1-al, 1,7-octadiene, 1,5-hexadiene, or 1,9-decadiene. There is no disclosure of the hydroformylation of butadienes or of the use of mono-phosphite or poly-phosphite ligands.

U.S. Pat. No. 4,248,802 discloses the hydroformylation of olefins with a catalyst consisting of a rhodium-containing aqueous solution of certain sulfonated triaryl phosphine ligands. Phosphite and poly-phosphite ligands are not disclosed. Example 24 of this patent discloses the hydroformylation of butadiene at 80° and 735 psi for 17 hours to give 75% $C_5$ aldehydes, with only a trace of $C_6$ dialdehydes.

Accordingly, it is an object of the present invention to provide a process for producing 1,6-hexanedials (e.g., adipaldehyde) by the hydroformylation of butadienes characterized by improved selectivity for the production of the 1,6-hexanedials.

SUMMARY OF THE INVENTION

This invention provides a hydroformylation process for producing a 1,6-hexanedial which comprises reacting a butadiene alkadiene with hydrogen and carbon monoxide in the presence of a catalytic amount of rhodium complexed with a poly-phosphite ligand having the formula:

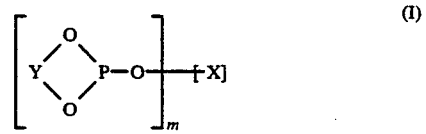

wherein Y is a divalent organic radical that contains at least 5 (preferably from 6 to 10) carbon atoms, X is an organic radical that contains at least 12 (preferably from 14 to 20) carbon atoms, that contains at least two branched alkyl groups and that has a valence of m supplied by carbon atoms of the X radical, provided that at least two of the carbon atoms supplying the valences of the X radical are separated from each other by no more than 10 (preferably by no more than 4) atoms and m has a value from 2 to 6 inclusive. Preferably Y in formula (I) above is monocyclic or polycyclic unsubstituted monovalent hydrocarbon radical and X is a monocyclic or polycyclic divalent hydrocarbon radical having the alkyl substituents indicated above.

The process of this invention achieves higher selectivities of butadienes to 1,6-hexanedials than have been achieved in prior art processes. Thus selectivities of butadienes to 1,6 hexanedials at least 10% and up to 85% are achieved by the process of this invention.

DETAILED DESCRIPTION OF THE INVENTION

The poly-phosphite ligands employed in the process of the present invention are those represented by formula (I) above. One class of preferred poly-phosphites employed in the process of the present invention have the formula:

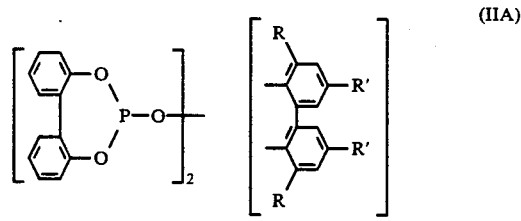

wherein R is a branched alkyl group (e.g., a isopropyl, tertiary butyl or tertiary amyl group and the like) and R' is an alkyl group or an alkoxy group (e.g., a methoxy, propoxy or butoxy group). Preferably R contains from 3 to 5 carbon atoms and R' contains from 1 to 4 carbon atoms.

Another preferred class of poly-phosphites within the scope of Formula (I) above employed in the process of the present invention have the formula:

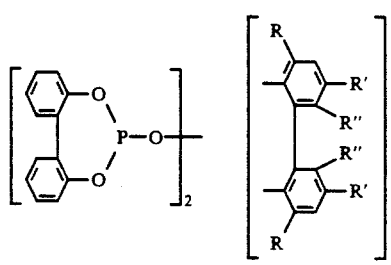
(IIB)

wherein R is as defined above, R' is hydrogen or an alkyl or alkoxy group (preferably containing 1 to 4 carbon atoms) and R" is hydrogen or alkyl group.

Ligands A, B, C and G shown below are ligands within the scope of formulas (I) and (IIA) above and are useful in the process of the present invention. Ligands M to Q shown below are ligands within the scope of Formulas (I) and (IIB) above and are also useful in the process of the present invention. The other ligands shown below are presented for purposes of comparison.

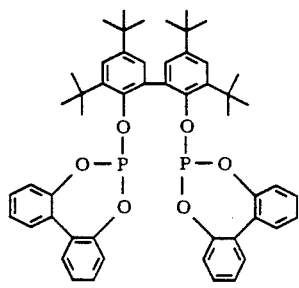
A

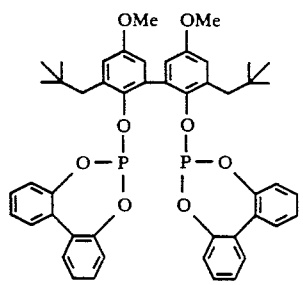
B

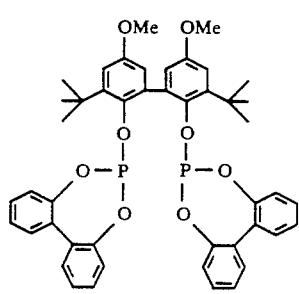
C

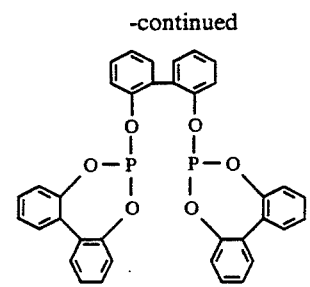
D

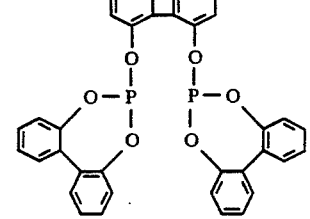
E

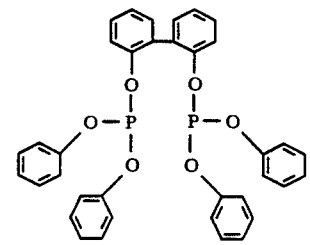
F

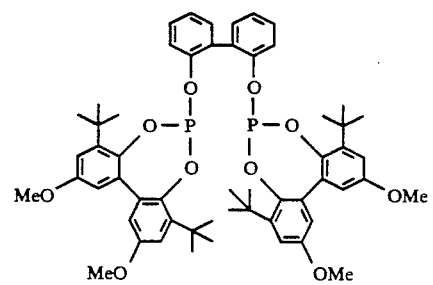
G

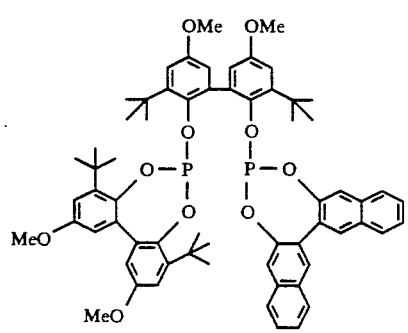
H

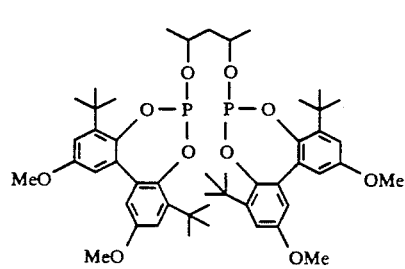
I

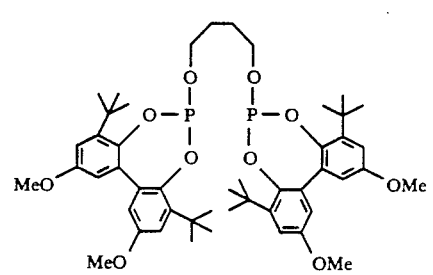

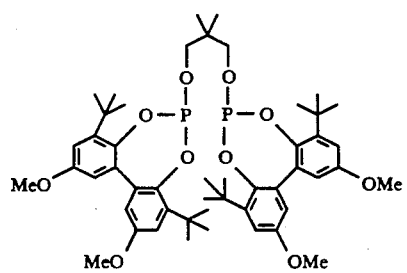
J
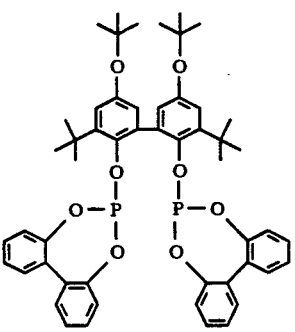
P
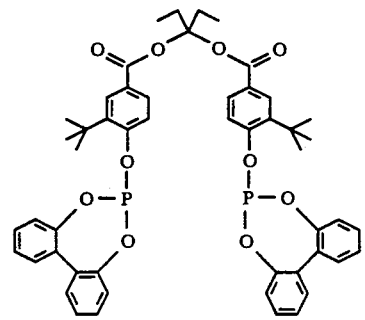
K
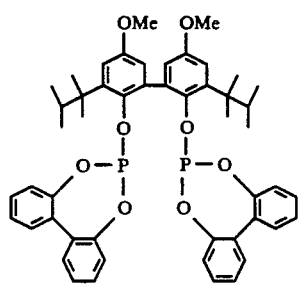
Q
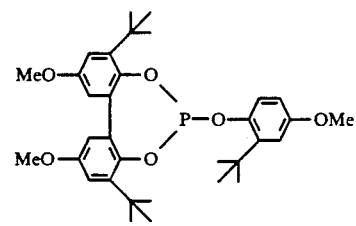
L
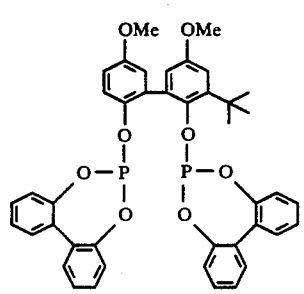
R
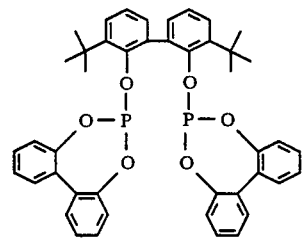
M
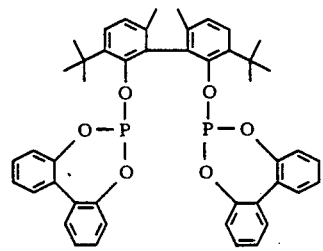
N
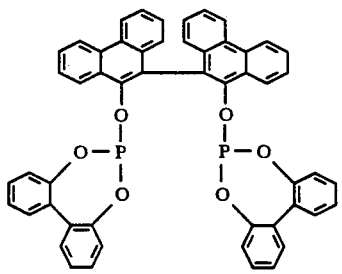
S
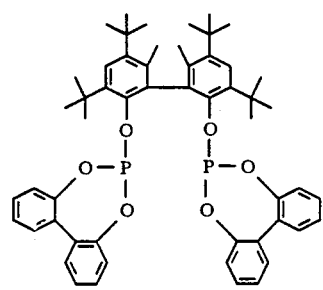
O
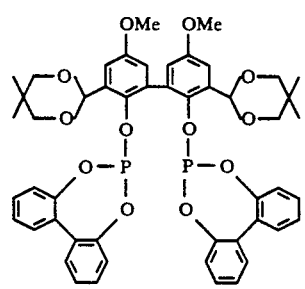
T -continued

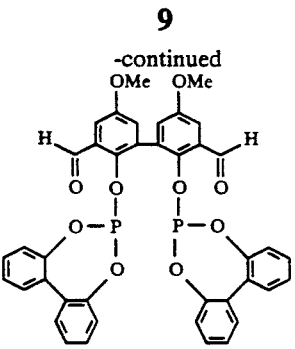
U

As is shown in the above formulas, Ligand A has tertiary butyl substituents, Ligand B has tertiary amyl substituents, Ligand N has tertiary butyl and methyl substituents, Ligand Q has tertiary hexyl substituents and Ligand T has methyl substituents. These alkyl substituents are shown by lines of characteristic shape in accordance with accepted practice. An allternative way of showing the alkyl substituents is by indicating their constivent atoms. Thus Ligand A and B can be alternatively shown as follows:

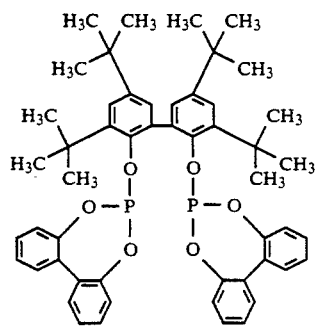

LIGAND A

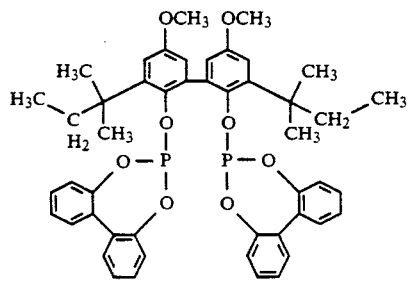

Ligand B

The valences in the radical represented by X in formula (I) above that link the X radical to the Y radicals are supplied by carbon atoms in the X radical. At least two of such carbon atoms must be separated from each other by no more than 10 atoms (preferably by no more than 4 atoms). In the case of formula (II) above, the carbon atoms of the X radical with the valences linking the X radical to the Y radicals are separated by 2 atoms. By way of illustration, in the case of operable Ligand A, the carbon atoms in question are separated by 2 atoms and are indicated by arrows in the formula of Ligand A shown below. By way of comparison, inoperable Ligand K has 11 atoms between the carbon atoms having similar valences. By way of illustration, the carbon atoms in question in Ligand K are indicated by arrows in the formula of Ligand K below. In addition, operable Ligands A, B and C have branched alkyl substituents on the polyvalent X radicals whereas inoperable Ligands D, E, F, H, I and J have no such substituents their similar polyvalent radicals. Inoperable Ligand L has no polyvalent radical [such as the X radical in formula (I) above] attached to two or more nonvalent radicals through phosphorus to oxygen bonds.

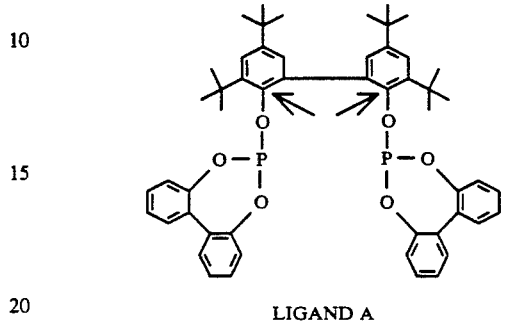

LIGAND A

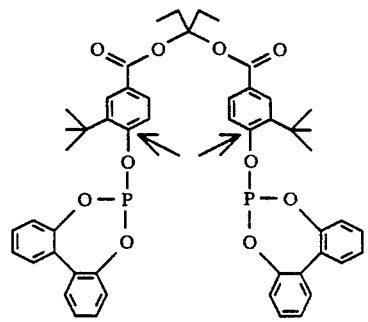

LIGAND K

In some cases, routine experimentation may be required to determine the best conditions in which to use a particular ligand in the practice of the process of the present invention (compare the results of Examples XXVII and LV below and the results of Examples XLIII and LVI below).

The ligands useful in the process of the present invention are known compositions. Such compositions and processes for their production are disclosed, for example, in U.S. Pat. No. 4,769,498. By way of illustration, Ligands A, B, and C were synthesized by reaction, in the presence of triethylamine, of two equivalents of 1,1'-biphenyl-2,2'-diylchlorophosphite ("biphenol chloridite") with the diol which becomes incorporated into the bridging group of the bis-phosphite, for example 1,1'-biphenyl-3,3'-di-t-butyl-5,5'-dimethoxy-2,2'-diol(- "iso-BHA diol") or 1,1'-biphenyl-3,3',5,5'-tetra-t-butyl-2,2'-diol ("iso-BHT diol"). Similarly, Ligand G was synthesized by reaction of one equivalent of isoBHA chloridite and one equivalent of binaphthol chloridite with isoBHA diol. The chlorophosphite complexes ("chloridites") were synthesized by reaction of phosphorus trichloride with a dialcohol, for example biphenol, binaphthol, or isoBHA diol. U.S. Pat. No. 4,769,498 broadly discloses and claims the use of such ligands in hydroformylation processes.

The poly-phosphite ligands described above are employed in this invention as both the phosphorus ligand of the rhodium complex catalyst, as well as the free phosphorous ligand that is preferably present in the reaction medium of the process of this invention. In addition, while the phosphorus Ligand of the rhodium poly-phosphite complex catalyst and excess free phosphorus ligand preferably present in a given process of this invention are normally the same polyphosphite ligand, different of poly-phosphite ligands, as well as mixtures of two or more different poly-phosphite ligands may be employed for each purpose in any given process, if desired.

The rhodium metal-poly-phosphorus complex catalysts employed in the present invention may be formed by methods known in the art. For instance, preformed rhodium metal hydrido-carbonyl-poly-phosphite catalysts may be prepared and introduced into the reaction mixture of a hydroformylation process. More preferably, the rhodium metal-poly-phosphite complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the poly-phosphite ligand for the in situ formation of the active catalyst. In a preferred embodiment of this invention, rhodium dicarbonyl acetylacetonate is employed as a rhodium precursor and reacted in the presence of a solvent with the poly-phosphite to form a catalytic rhodium-polyphosphite complex precursor which is introduced into the reactor along with excess free poly-phosphite Ligand for the in situ formation of the active catalyst. In any event, it is sufficient for the purpose of this invention that carbon monoxide, hydrogen and poly-phosphite are all Ligands that are capable of being complexed with the rhodium metal and that an active rhodium metal poly-phosphite catalyst is present in the reaction mixture under the conditions used in the hydroformylation process.

More particularly, in the process of the present invention, a catalyst precursor composition can be formed consisting essentially of a solubilized rhodium metal-poly-phosphite complex precursor catalyst, an organic solvent and free poly-phosphite ligand. Such precursor compositions may be prepared by forming a solution of a rhodium metal starting material, such as a metal oxide, hydride, carbonyl or salt, e.g. a nitrate, which may or may not be in complex combination with a poly-phosphite ligand as defined herein. Any suitable rhodium metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and poly-phosphite rhodium carbonyl hydrides. Carbonyl and poly-phosphite ligands, if not already complexed with the initial rhodium metal, may be complexed to the metal either prior to or in situ during the carbonylation process. By way of illustration, the preferred catalyst precursor composition of this invention consists essentially of a solubilized rhodium carbonyl poly-phosphite complex precursor catalyst, an organic solvent and free poly-phosphite ligand prepared by forming a solution of rhodium dicarbonyl acetylacetonate, an organic solvent and a poly-phosphite ligand as defined herein. The poly-phosphite readily replaces one of the dicarbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium poly-phosphite complex precursor are soluble can be employed. Accordingly, the amounts of rhodium complex catalyst precursor, organic solvent and poly-phosphite, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or poly-phosphite ligand, to form the active rhodium complex catalyst as explained above. The acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions thus provides a simple economical and efficient method for handling the rhodium precursor metal and hydroformylation start-up.

Accordingly, the rhodium metal-poly-phosphite complex catalysts used in the process of this invention consists essentially of the rhodium metal complexed with carbon monoxide and a poly-phosphite ligand, said ligand being bonded (complexed) to the rhodium in a chelated and/or non-chelated fashion. Moreover, the terminology "consists essentially of", as used herein, does not exclude, but rather includes, hydrogen complexed with the metal, in addition to carbon monoxide and the poly-phosphite ligand. Further, such terminology does not exclude the possibility of other organic Ligands and/or anions that might also be complexed with the metal. Materials in amounts which unduly adversely poison or unduly deactivate the catalyst are not desirable and so the catalyst most desirably is free of contaminants such as rhodium-bound halogen (e.g., chlorine, and the like) although such may not be absolutely necessary. The hydrogen and/or carbonyl ligands of an active rhodium-poly-phosphite complex catalyst may be present as a result of being ligands bound to a precursor catalyst and/or as a result of in situ formation, e.g., due to the hydrogen and carbon monoxide gases employed in hydroformylation process of the present invention.

The amount of complex catalyst present in the reaction mixture used in the process of this invention need only be that minimum amount necessary to provide the desired rhodium metal concentration to catalyze the hydroformylation reaction. In general, rhodium metal concentrations in the range of from about 10 parts per million by weight to about 1000 parts per million by weight, calculated as free metal, should be sufficient for most carbonylation processes. Moreover, in the rhodium catalyzed hydroformylation processes of this invention, it is generally preferred to employ from 100 to 500 parts per million of rhodium by weight calculated as free metal based on the weight of the total reaction mixture.

The butadiene starting materials useful in the process of the present invention are conjugated aliphatic olefins having the structure:

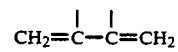

The butadienes can be linear or branched and can contain substituents (e.g., alkyl groups, halogen atoms, amino groups or silyl groups). Illustrative of suitable butadiene starting materials are butadiene, isoprene and dimethyl butadiene. Most preferably, the butadiene starting material is butadiene itself ($CH_2=CH-CH=CH_2$).

In one embodiment of the process of the present invention, an alpha-mono-olefin is hydroformylated along with a butadiene using the above-described rhodium/ligand complex catalysts. In such cases, an aldehyde derivative of the alpha-mono-olefin is also produced along with the 1,6-hexanedial. It has been found that the butadiene reacts to form a complex with rhodium more rapidly than the alpha-mono-olefin and requires more forcing conditions to be hydroformylated itself. Further, when the process of this invention is conducted at 95° C. and a total pressure of 500 psi, the alpha-mono-olefin are hydroformylated in the presence of the butadiene but at a much slower rate than would have been expected based on the prior art. Thus, hydroformylation of butadiene under ethylene pressure produced propionaldehyde at a rate of 1.6 mol/l-hr whereas, based on the prior art, at this temperature ethylene hydroformylation would have been expected to be too fast to measure. The butadiene selectivity to adipaldehyde in this reaction (i.e., coreaction with ethylene) was unchanged. Similarly, hydroformylation of a solution containing 50% butadiene and 50% 1-hexene produced heptanal at a rate of 0.6 mol/l-hr whereas, based on the prior art, the rate of hydroformylation of the 1-hexene would have been expected to be too fast to measure under such conditions. Again the selectivity to adipaldehyde remained the same as when no alpha-mono-olefin was present.

However, it has been found that, when 2-hexene was added to a butadiene hydroformylation reaction mixture, the 2-hexene did not react at all and the butadiene reacted to produce only valeraldehyde. In a control experiment, 2-hexene alone was hydroformylated at a rate of 0.5 mol/l-hr. It is evident from the above findings that butadiene is a catalyst inhibitor but only under mild conditions. It appears that, because of the tendency of butadiene to coordinate to rhodium to form a relatively inert complex, alpha-mono-olefins olefins are unable to react, except under the high CO partial pressures (e.g., from 250 to 500 psi) required to force the butadiene to react. These results are surprising in view ofthe disclosure of publication (c) discussed above (i.e., Journal of Molecular Catalysis, 1985, 31, 345-353, "The Hydroformylation of Butadiene Catalyzed by Rhodium-Diphosphine Complexes").

The hydroformylation process of this invention is preferably conducted in the presence of an organic solvent for the rhodium metal-polyphosphite complex catalyst. Any suitable solvent which does not unduly adversely interfere with the intended hydroformylation process can be employed. Such solvents include those heretofore commonly employed in known rhodium metal-catalyzed hydroformulation processes. By way of illustration, suitable solvents include those disclosed in U.S. Pat. Nos. 3,527,809 and 4,148,830. Mixtures of one more different solvents may be employed if desired. In general, it is preferred to employ aldehyde solvent corresponding to the aldehyde products desired to be produced and/or higher boiling aldehyde liquid condensation by-products of such aldehydes as the primary solvent, such as the higher boiling aldehyde liquid condensation by-products of such aldehydes that are produced in situ during the hydroformylation process. While any suitable solvent may be employed at the start up of a continuous process, the primary solvent will normally eventually comprise both aldehyde products and higher boiling aldehyde liquid condensation by-products due to the nature of such continuous processes. Such aldehyde condensation by-products can also be preformed if desired. Methods for the preparation of higher boiling aldehyde condensation by-products are more fully described in U.S. Pat. Nos. 4,148,830 and 4,247,486.

Under the conditions used in the Examples appearing below,
tetrahydrofuran,
toluene,
diglyme (i.e., ethylene glycol dimethyl ether),
"DMF" (i.e., N,N-dimethyl formamide),
"NMP" (i.e., N-methylpyrrolidone), and
t-butanol
were found to be useful in the process of the present invention to achieve an improved selectivity to 1,6-hexanedials whereas
sulfolane,
tetraglyme (i.e., tetraethylene glycoldimethyl ether), and
"DMEU (i.e. dimethylethylene urea)
were not useful for that purpose.

The properties of these specific solvents are as follows:

|  | Dielectric Constant (E) | Boiling Point* (°C.) |
| --- | --- | --- |
| Preferred |  |  |
| THF | 7.6 | 65° |
| Toluene | 2.4 | 111° |
| tBuOH | 10.9 | 82° |
| Useful |  |  |
| Diglyme | 7.3 | 162° |
| DMF | 36.7 | 153° |
| NMP | 37.7¹ | 81°/10 mm Hg |
| Not Useful |  |  |
| Sulfolane | 43.0 | 285° |
| Tetraglyme | 7.7 | 275° |
| DMEU | 25.0 | 108°/17 mm Hg |

*At atmospheric pressure unless otherwise indicated.

Hence the preferred solvents have dielectric constants of less than 30 and atmospheric boiling points of less than 150° C. and most preferred solvents have dielectric constants of less than 15 and atmospheric boiling points of less than 120° C. In general, the amount of solvent, when employed in the process of the present invention, may range from about 5 percent by weight up to about 95 percent by weight or more based on the total weight of the reaction medium.

It is also generally preferred to carry out the hydroformylation process of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the rhodium metal-poly-phosphite catalyst, and free poly-phosphite ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). However, it is generally desirable to employ a continuous process that involves either a liquid and/or gas recycle procedure. Such types of recycle procedure are well known in the art and may involve the liquid recycling of the rhodium metal-phosphite complex catalyst solution separated from the desired aldehyde reaction product(s), such as disclosed e.g., in U.S. Pat. No. 4,148,830 or a gas cycle procedure such as disclosed e.g., in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

At the conclusion of (or during) the process of this invention, the desired 1,6-hexanedial product may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing alkanedial product, catalyst, etc.) removed from the reactor can be passed to a vaporizer/separator wherein the desired aldehyde product can be separated via distillation, in one or more stages, under normal, reduced or elevated pressure, from the liquid reaction solution, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed alkanedial product, e.g., by distillation in any conventional manner. It is generally desirable to employ a phosphorus ligand whose molecular weight exceeds that of the higher boiling aldehyde trimer by-product corresponding to the 1,6-hexanedial being produced in the hydroformylation process in order to avoid or at least minimize possible Ligand loss during removal via distillation of the 1,6-hexanedial product and/or higher boiling aldehyde condensation byproducts, from the reaction mixture. Another suitable recovery technique is solvent extraction. In general, it is preferred to separate the desired 1,6-hexanedial product from the rhodium catalyst-containing reaction mixture under reduced pressure and at low temperatures so as to avoid possible degradation of the polyphosphite Ligand and reaction (e.g., cyclization) of the 1,6-hexanedial product. When an V-mono-olefin reactant is also employed, the aldehyde derivative thereof can also be separated by the above methods.

The hydroformylation process of this invention is preferably carried out in the presence of free poly-phosphite ligand, i.e., ligand that is not complexed with the rhodium metal of the rhodium metal complex catalyst employed. Thus the free poly-phosphite ligand may correspond to any of the above-desired polyphosphite ligands discussed above. However, while it is preferred to employ a free poly-phosphite ligand that is the same as the poly-phosphite ligand of the rhodium metal-poly-phosphite complex catalyst such ligands need not be the same in a given process, but can be different if desired. While the hydroformylation process of this invention may be carried out in any excess amount of free poly-phosphite ligand desired, e.g., at least one mole of free poly-phosphite ligand per mole of rhodium metal present in the reaction medium, the employment of free poly-phosphite ligand may not be absolutely necessary. Accordingly, in general amounts of poly-phosphite ligand of from about 1 to about 15, and preferably from about 5 to about 8, moles per mole of rhodium metal present in the reaction medium should be suitable for most purposes. The above-mentioned amounts of poly-phosphite ligand employed being the sum of both the amount of poly-phosphite that is bound (complexed) to the rhodium metal present and the amount of free (non-complexed) poly-phosphite ligand present. If desired, make-up polyphosphite ligand can be supplied to the reaction mixture used in of the hydroformylation process at any time during the process and in any suitable manner to maintain a predetermined level of free ligand in the reaction mixture.

The reaction conditions for effecting a hydroformylation process of this invention include reaction temperatures of from about 50° C. to about 150° C. (preferably 75° C. to 110° C.) and total pressures from about 200 to 1,000 psig (preferably 500 to 1000 psig). The reaction temperature employed in a given process will of course be dependent upon the particular olefinic starting material and metal catalyst employed as well as the efficiency desired. The partial pressure of hydrogen is from 100 to 500 psig (preferably from 200 to 300 psig) and the partial pressure of carbon monoxide is from 100 to 1000 psig (preferably from 200 to 700 psig). In general, the molar ratio of hydrogen to carbon monoxide may range from about 1:10 to 100:1 or higher, the more preferred hydrogen to carbon monoxide molar ratio being from about 1:1 to about 10:1.

Particularly when conducting the process of the present invention in a continuous liquid recycle mode, undesirable acidic by-products (e.g., a hydroxy alkyl phosphonic acid) may result due to reaction of the phosphite Ligand and the 1,6-hexanedial product over the course of the process. The formation of such byproducts undesirably lowers the concentration of the Ligand. Such acids are often insoluble in the reaction mixture and such insolubility can lead to precipitation of an undesirable gelatinous by-product and may also promote the autocatalytic formation of further acidic byproducts. The polyphosphite Ligands used in the process of this invention have good stability against the formation of such acids. However, if this problem does occur, the liquid reaction effluent stream of a continuous liquid recycle process may be passed, prior to (or more preferably after) separation of the desired alkanedial product therefrom, through any suitable weakly basic anion exchange resin, such as a bed of amine Amberlyst ® resin, e.g., Amberlyst ® A-21, and the like, to remove some or all of the undesirable acidic by-products prior to its reincorporation into the hydroformylation reactor. If desired, more than one such basic anion exchange resin bed, e.g. a series of such beds, may be employed and any such bed may be easily removed and/or replaced as required or desired. Alternatively if desired, any part or all of the acid-contaminated catalyst recycle stream may be periodically removed from the continuous recycle operation and the contaminated liquid so removed treated in the same fashion as outlined above, to eliminate or reduce the amount of acidic by-product prior to reusing the catalyst containing liquid in the hydroformylation process. Likewise, any other suitable method for removing such acidic byproducts from the hydroformylation process of this invention may be employed herein if desired such as by extraction of the acid with a weak base (e.g., sodium bicarbonate).

In the process of this invention, the overall hydroformylation reaction generally proceeds in two stages. In the first stage, the butadiene is converted to an unsaturated aldehyde (i.e., a 3-pentenal). In the second stage, the 3-pentenal isomerizes to a 1-alkenal which can be readily further hydroformylated to a 1,6-hexanedial. The 3-pentenal produced in the first stage is also capable of a side reaction, i.e., isomerization to an a,β-pentenal. Such a,β-pentenals are relatively inert to further hydroformylation but fairly readily hydrogenate to produce undesirable pentanals. In the case of the hydroformylation of butadiene itself, these reactions are illustrated by the following equation:

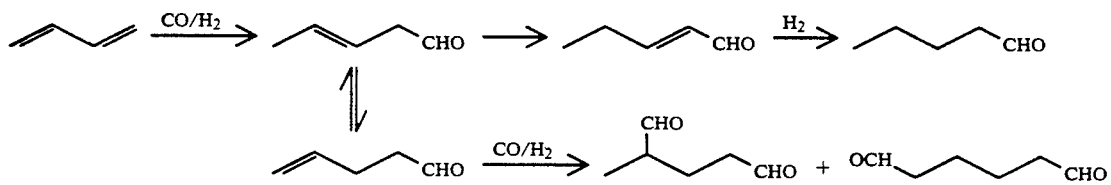

The undesirable isomerization of the 3-pentenal to form V,β-pentenals can be significantly retarded by converting the 3-pentenal to an acetal by reaction of the 3-pentenal with a 1,2-diol, a 1,3-diol, or a 2,4-diol, preferably in the presence of an acetalization catalyst. Water is formed as a byproduct in the acetylization reaction and may undergo undesirable reaction with the ligand. Hence the acetals is preferably separated from the water. Then the acetal can be readily hydroformylated further to produce a mono-acetal of the desired 1,6-hexanedial. The mono-acetal is readily converted to a 1,6-alkanedial by hydrolysis with an acid catalyst. Suitable diols for use in forming the acetals of the 3-pentenal are ethylene glycol, 2,3-butanediol, 2,3-dimethyl-2,3-butanediol (pinacol) and 2,4-pentanediol and suitable acetalization catalysts are acidic compounds such as pyridinium tosylate, concentrated sulfuric acid, Amberlyst ® resins, phosphoric acid and like. Hydrous zirconium oxide was not found to be a suitable catalyst.

Accordingly, in a preferred embodiment, this invention provides a hydroformylation process for producing a 1,6-hexanedial which comprises:

(A) reacting a butadiene with hydrogen and carbon monoxide in the presence of a catalytic amount of rhodium complexed with a poly-phosphite ligand represented by formula (I) above to produce a 3-pentenal (i.e., an unsaturated mono-aldehyde derivative of the butadiene);

(B) separating the 3-pentenal from the rhodium catalyst before any substantial amount of a,β-pentenal has formed (e.g., before 10 weight percent, or preferably before 1 weight percent, of the a,β-pentenal has formed based on the total amount of 3-pentenal present);

(C) reacting the 3-pentenal with a 1,2-diol, a 1,3-diol or a 2,4-diol, preferably in the presence of an acetalization catalyst, to produce an acetal of the 3-pentenal and water;

(D) (optionally) separating the acetal of the 3-pentenal from the water;

(E) reacting the acetal of the 3-pentenal with hydrogen and carbon monoxide in the presence of a catalytic amount of rhodium complexed with a poly-phosphite ligand represented by formula (I) above to produce a mono-acetal of the 1,6-hexanedial; and (F) converting the monoacetal to the 1,6-hexanedial.

The above-described preferred embodiment of this invention further increases conversion of the butadiene to the 1,6-hexanedial by reducing the formation both of the a,β-pentenals (which form by isomerization of the 3-pentenal) and of alkanols derived from such a,β-pentenals. Conversions to about 85% of 1,6-hexanedials can be achieved by employing this preferred embodiment.

When the process of this invention is conducted in two stages (i.e., first producing a 3-pentenal under one set of conditions and then producing an 1,6-hexanedial from the 3-pentenal (or its acetal) under another set of conditions), it is preferred to conduct the first stage at a temperature from 75° C. to 110° C. and at a total pressure from 500 psi to 1000 psi and to conduct the second stage at a temperature from 100° C. to 120° C. and at a pressure from 700 psi to 1000 psi. Rhodium complexed with a poly-phosphite ligand represented by formula (I) above is used in both stages. The other conditions can be the same in both stages.

It is also possible to increase the butadiene selectivity to the desired 1,6-hexanedial (e.g., to achieve about 45% selectivity) by conducting the first hydroformylation stage in the presence of a suitable diol (described above) to achieve acetylization along with hydroformylation so as to produce directly the acetal of the 1,6-hexanedial. The acetal can then be further reacted as in steps (D) and (E) above to produce the desired 1,6-hexanedial. However, in such cases the poly-phosphite ligand may undergo undesirable side reactions during the first stage with the water formed in the acetalization reaction.

The 1,6-hexanedial products of the hydroformylation process of this invention (e.g., adipaldehyde) have a wide range of utilities that are well known in the art, e.g., they are useful as starting materials for the production of alcohols (e.g., 1,6-hexanediol) and acids (e.g., adipic acid) by known processes.

PREPARATION OF LIGANDS

Ligand P was synthesized by reaction of 1,1'-biphenyl-3,3'-di-t-butyl-5,5'-di-t-butoxy-2,2'-diol with two equivalents of biphenol chloridite. A 100 mL Schlenk flask was charged with 8 mL toluene solvent, 2 mL pyridine, and 0.80 g biphenol chloridite (2.36 mmol), placed under a nitrogen atmosphere, and cooled to −5° C. in a dry ice/acetone bath. A 100 mL Schlenk flask was charged with 8 mL toluene solvent and 0.50 g of the diol (1,14 mmol) and placed under a nitrogen atmosphere. This solution was added to the chilled chloridite solution via syringe over 10 minutes. The reaction was warmed to room temperature and stirred for 16 hours. The solution was then filtered through a Schlenk frit under nitrogen to remove pyridinium chloride. The solution was concentrated to a yellow syrup on a rotary evaporator, and 15 mL acetonitrile was added to precipitate the bisphosphite ligand. The mixture was stirred an additional 2 hours at room temperature and filtered. The solids were washed with acetonitrile and dried under vacuum.

Follow procedures similar to the above-described procedure, the following ligands were produced from the following starting materials:

| Ligand | Diol | Chloridite |
|---|---|---|
| A | 1,1'-biphenyl-3,3',5,5'-tetra-t-butyl-2,2'-diol | 1,1'-biphenyl-2-2'-diylchlorophosphite ("biphenol chloridite") |
| B | 1,1'-biphenyl-3,3'-di-t-amyl-5,5'-dimethoxy-2,2'-diol | Biphenol chloridite |
| C | 1,1'-biphenyl-3,3'-di-t-butyl-5,5'-dimethoxy-2,2'-diol | Biphenol chloridite |
| D | 2,2'-biphenol | Biphenol chloridite |
| E | 2,2'-biphenol | Diphenylchlorophosphite |
| F | 2,2'-biphenol | 1,1'-biphenyl-3,3'-di-t-butyl-5,5'-dimethoxy-2,2'-diylchlorophosphite ("iso-BHA chloridite") |
| G | 1,1'-biphenyl-3,3'-di-t-butyl-5,5'-dimethoxy-2,2'-diol | iso-BHA chloridite; 2,2'-binaphthylchlorophosphite |
| H | 2,4-pentanediol | iso-BHA chloridite |
| I | 1,4-butanediol | iso-BHA chloridite |
| J | 2,2-dimethyl-1,3-propanediol | iso-BHA chloridite |
| K | 3,3-di(3-t-butyl-4-hydroxybenzoyl)pentane | Biphenol chloridite |
| L | 1,1'-biphenyl3,3'-di-t-butyl-5,5'-dimethoxy-2,2'-diol | 3-t-butyl-5-methoxyphenyl-dichlorophosphite |
| M | 1,1'-biphenyl-3,3'-di-t-butyl-2,2'-diol | Biphenol chloridite |
| N | 1,1'-biphenyl-3-3'-di-t-butyl-6,6'-dimethyl-2,2'-diol | Biphenol chloridite |
| O | 1,1'-biphenyl-3,3',5,5'-tetra-t-butyl-6,6'-dimethyl-2,2'-diol | Biphenol chloridite |
| P | 1,1'-biphenyl-3,3'-di-t-butyl-5,5'-di-t-butoxy-2,2'-diol | Biphenol chloridite |
| Q | 1,1'-biphenyl-3,3'-di-t-hexyl-5,5'-dimethoxy-2,2'-diol | Biphenol chloridite |
| R | 1,1'-biphenyl-3-t-butyl-5,5'-dimethoxy-2,2'-diol | Biphenol chloridite |
| S | 2,2'-biphenanthrol | Biphenol chloridite |
| T | 1,1'-biphenyl-3,3'-di[2-(1,3-dioxacyclohexane)]-5,5'-dimethoxy-2,2'-diol | Biphenol chloridite |
| U | 1,1'-biphenyl-3,3'-di-formyl-5,5'-dimethoxy-2,2'-diol | Biphenol chloridite |

The following Examples are illustrative of the present invention and are not to be regarded as limiting.

In the Examples appearing below, the following abbreviations have the indicated meanings:

| | |
|---|---|
| rate | gram-mols per liter per hour |
| mL | milliliter |
| ppm | parts per million (by weight) |
| % | weight percent |
| g | grams |
| acac | acetylacetonate |
| CO:H$_2$ | ratio of CO to H on a mol basis |
| syngas | a mixture of CO and H$_2$ |
| conv. | conversion, i.e. percent butadiene converted to aldehydes |
| selectivity | the weight of a specific aldehyde product divided by the weight of all the aldehyde products and multiplied by 100. |
| ligand/rhodium (L/Rh) | ratio of ligand to rhodium on a mol basis |
| mol/-hr | mols per liter-hour |
| psig | pounds per square inch gauge pressure |
| butadiene | CH$_2$=CH—CH=CH$_2$ |
| isoBHA | butylated hydroxylanisole |

EXAMPLE I

A catalyst solution consisting of 0.019 g Rh(CO)(acac)(300 ppm rhodium), 85 g Ligand A (14:1 Ligand A to rhodium ratio), 2.2 g N-methylpyrrolidone (as an internal standard for gas chromatography), and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 CO:H ("syn gas"). The reaction rate was determined by monitoring the rate of syngas consumption. The rate of reaction was found to be 1.7 mol/1-hr. After two hours of reaction, the solution was analyzed by gas chromatography to determine its composition. Butadiene was 92% converted to various products. The products consisted of 61% valeraldehyde, 1% pentenals, 11% branched dialdehyde and 25% adipaldehyde.

EXAMPLES II TO XVII

Table I below summarizes other hydroformylation reactions employing Ligand A/rhodium catalyst for butadiene hydroformylation. All the reactions were conducted in tetrahydrofuran solvent following the general procedure used in Example 1 above. In all except three Examples (denoted by ** in Table I), adipaldehyde selectivities are superior to those obtained by the prior art processing described above.

TABLE I

| Example | Rh (ppm) | Ligand/ Rhodium | Temp. (°C.) | Total Pressure (psig) | CO—H$_2$ | Rate | Conv. | Selectivities | |
|---|---|---|---|---|---|---|---|---|---|
| | | | | | | | | Pentenals | Adipaldehyde |
| II | 150 | 12 | 95° | 500 | 1 | 0.6 | 82% | 71% | 16% |
| III | 600 | 14 | 95° | 500 | 1 | 2.8 | 90% | — | 16% |
| IV** | 300 | 1 | 95° | 500 | 1 | 0.2 | 77% | 85% | 6 |
| V | 300 | 4 | 95° | 500 | 1 | 2.2 | 97% | 68% | 19% |
| VI | 300 | 40 | 95° | 500 | 1 | * | 79% | 60% | 13% |
| VII** | 300 | 14 | 50° | 500 | 1 | 0.5 | 99% | 96% | 0% |
| VIII | 300 | 14 | 75° | 500 | 1 | 1.0 | 99% | 4% | 26% |
| IX | 300 | 14 | 120° | 500 | 1 | * | 95% | 1% | 17% |
| X** | 300 | 14 | 95° | 100 | 1 | * | <5% | 0% | 0% |
| XI | 300 | 14 | 95° | 1000 | 1 | 6.3 | 90% | 43% | 24% |

TABLE I-continued

| Example | Rh (ppm) | Ligand/ Rhodium | Temp. (°C) | Total Pressure (psig) | CO—H$_2$ | Rate | Conv. | Selectivities Pentenals | Adipaldehyde |
|---|---|---|---|---|---|---|---|---|---|
| XII | 300 | 14 | 95° | 500 | 1.9 | 1.1 | 99% | 34% | 21% |
| XIII | 300 | 14 | 95° | 500 | 4 | 0.9 | 90% | 84% | 10% |
| XIV | 300 | 14 | 95° | 500 | 0.5 | 1.3 | 98% | 0% | 19% |
| XV | 300 | 14 | 95° | 700 | 1.8 | 4.8 | 99% | 21% | 25% |
| XVI | 300 | 14 | 95° | 900 | 4 | 2.7 | 95% | 43% | 25% |
| XVII | 300 | 14 | 110° | 900 | 4 | 3.0 | 99% | 10% | 30% |

*Not determined.
**No improvement in selectivity to adipaldehyde as compared to the above-described prior art (Comparative Example).

EXAMPLES XVIII TO XXV

Table II below shows the results of reactions in solvents using the following hydroformylation conditions: 300 ppm Rh, Ligand A: Rh ratio equals 14, 95° C. reaction temperature, 500 psi total pressure, 1:1 CO:H$_2$ and 2 hour reaction time.

TABLE II

| Example | Solvent | Conversion* | Selectivity Pentenals | Adipaldehyde |
|---|---|---|---|---|
| XVIII | toluene | 98% | 7% | 23% |
| XIX | diglyme | 97% | 36% | 12% |
| XX | DMF | 99% | 3% | 15% |
| XXI** | sulfolane | 42% | 80% | 2% |
| XXII** | tetraglyme | 91% | 80% | 4% |
| XXIII** | DMEU | 67% | 86% | 2% |
| XXIV | NMP | 95% | 28% | 11% |
| XXV | t-butanol | 98% | 1% | 26% |

*Of butadiene to mono- and di-aldehydes
**Comparative Example. Adipaldehyde selectivity lower than obtained in the above-described prior art.

Examples XXVI to XXIX below illustrate the use of various ligands for butadiene hydroformylation.

EXAMPLE XXVI

Butadiene Hydroformylation with Ligand B/Rhodium Catalyst

A catalyst solution consisting of 0.012 g Rh(CO)$_2$-(acac)(200 ppm rhodium), 0.47 g Ligand B (12:1 ligand to rhodium ratio) and 15 mL tetrahydrofuran was charged to a 100 mL Parr reactor. Butadiene (2 mL) was charged to the reactor as a liquid under pressure. The reaction was heated to 95° C. and pressurized to 500 psig with 1:1 CO:H$_2$. The reaction rate was determined by monitoring the rate of syn gas (CO and H) consumption. The rate of reaction was found to be 0.4 mol/l-hr. After two hours of reaction the solution was analyzed by gas chromatography to determine product composition. Butadiene was 95% converted. The products consisted of 7% valeraldehyde, 82% pentenals, 1% branched dialdehyde, and 10% adipaldehyde.

EXAMPLE XXVII (Comparative)

Hydroformylation of Butadiene with Ligand C/Rhodium Catalyst

A catalyst solution consisting of 0.012 g Rh(CO)$_2$-(acac)(200 ppm rhodium), 0.47 g Ligand C (14:1 Ligand C to rhodium ratio), and 15 mL tetrahydrofuran was charged to a 100 mL Parr reactor. Butadiene (2 mL) was charged to the reactor as a liquid under pressure. The reaction was heated to 95° C. and pressurized to 500 psig with 1:1 CO:H$_2$. The reaction rate was determined by monitoring the rate of syngas consumption. The rate of reaction was found to be 1.2 mol/l-hr. After two hours of reaction the solution was analyzed by gas chromatography to determine product composition. Butadiene was 68% converted. The products consisted of 8% valeraldehyde, 72% pentenals, 1% branched dialdehyde and 5% adipaldehyde. Ligand C gives good conversions under the conditions of Example LV below.

EXAMPLE XXVIII (Comparative)

Hydroformylation of Butadiene with (isoBHA-P)(Binaphthyl-P)(isoBHA diol)[Ligand G]/Rhodium Catalyst A catalyst solution consisting of 0.019 g Rh(CO)$_2$-(acac)(300 ppm rhodium), 0.88 g Ligand G (11:1 Ligand G to rhodium ratio), and 25 mL tetrahydrofuran was charged to a 1000 mL Parr reactor. Butadiene (3 mL) was charged to the reactor as a liquid under pressure. The reaction was heated to 95° C. and pressurized to 500 psig with 1:1 CO:H$_2$. Only a small amount of syngas was taken up by the solution. After two hours of reaction the solution was analyzed by gas chromatography to determine product composition. Butadiene was 33% converted. The products consisted of 4% valeraldehyde and 75% pentenals. No dialdehydes were found in the analysis.

EXAMPLE XXIX

Hydroformylation of Butadiene with (isoBHA-P)$_2$-1,4-butanediol[Ligand I]/Rhodium Catalyst A catalyst solution consisting of 0.019 g Rh(CO)$_2$-(acac)(300 ppm rhodium), 0.88 g Ligand I (13:1 Ligand I to rhodium ratio), 2.5 g NMP (as an internal standard) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 CO:H$_2$. Only a small amount of syngas was taken up by the solution. After two hours of reaction the solution was analyzed by gas chromatography to determine product composition. Butadiene was less than 5% converted, and the products consisted of only pentenals. No dialdehydes were found by analysis.

Examples XXX to XXXIII below illustrate the formation of aldehyde acetals using various diols. All reactions were run with 300 ppm rhodium and Ligand A: rhodium ratio = 14.

EXAMPLE XXX

Butadiene Hydroformylation in THF/Ethylene Glycol

A catalyst solution was prepared in 12.5 mL THF, 12.5 mL ethylene glycol (7 mol diol/mole butadiene), and charged to a 100 mL Parr reactor. Butadiene (3 mL) was added to the reactor as a liquid under pressure. The mixture was heated to 110° C. and pressurized to 850 psi with 4:1 CO:H$_2$. The reaction rate was followed by monitoring the syn gas uptake. Syngas (1:1 CO:H$_2$) was periodically recharged to the reactor to maintain a constant pressure at 850 psi. The initial reaction rate was found to be 4.5 mol/1-hr. After two hours reaction time the mixture was analyzed by gas chromatography to determine the product composition. The products consisted of 32% C5 acetals, 15% diacetals of branched C6 dialdehydes and 49% adipaldehyde acetals.

EXAMPLE XXXI

Butadiene Hydroformylation in THF/1.3-Propanediol

A catalyst solution was prepared in 13 mL THF, 12 mL 1.3-propanediol (5 mol diol/mole butadiene) and charged to a 100 mL Parr reactor. Butadiene (3 mL) was added to the reactor as a liquid under pressure. The mixture was heated to 110° C. and pressurized to 900 psi with 4:1 CO:H$_2$. The reaction rate was followed by monitoring the syngas uptake. Syngas (1:1 CO:H$_2$) was periodically recharged to the reactor to maintain a constant pressure at 900 psi. The initial reaction rate was found to be 8.3 mol/1-hr. After two hours reaction time the mixture was analyzed by gas chromatography to determine the product composition. The products consisted of 39% aldehyde acetals, 9% diacetals of branched C6 dialdehydes and 36% adipaldehyde acetals.

EXAMPLE XXXII (Comparative)

Butadiene Hydroformylation in THF/1.4-Butanediol

A catalyst solution was prepared in 18 mL 1,4-butanediol (2 mol diol/mole butadiene) and charged to a 100 mL Parr reactor. Butadiene (3 mL) was added to the reactor as a liquid under pressure. The mixture was heated to 95° C. and pressurized to 500 psi with 1:1 CO:H$_2$. The reaction rate was followed by monitoring the syngas uptake. The initial reaction rate was found to be 3.0 mol/1-hr. After two hours reaction time the mixture was analyzed by gas chromatography to determine the product composition. The products consisted of 76% valeraldehyde, 13% branched C$_6$ aldehydes and 11% valeraldehyde acetal.

EXAMPLE XXXIII

Butadiene Hydroformylation in THF/2,3-Butanediol

A catalyst solution was prepared in 13 mL THF, 12 mL 2,3-Butanediol (4 mol diol/mole butadiene) and charged to a 100 mL Parr reactor. Butadiene (3 mL) was added to the reactor as a liquid under pressure. The mixture was heated to 110° C. and pressurized to 800 psi with 4:1 CO:H$_2$. The reaction rate was followed by monitoring the syngas uptake. Syngas (1:1 CO:H$_2$) was periodically recharged to the reactor to maintain a constant pressure at 900 psi. The initial reaction rate was found to be 5.0 mol/1-hr. After two hours reaction time the mixture was analyzed by gas chromatography to determine the product composition. Approximately 47% of the products were aldehydes, of these, 61% was valeraldehyde, 6% branched dialdehyde, and 13% adipaldehyde. Approximately 53% of the products were acetals; these consisted of 62% valeraldehyde acetal and 32% adipaldehyde acetal.

Examples XXXIV to XXXVI below illustrate the use of an acetalization catalyst to increase the yield of acetals at low diol/butadiene ratios. The reaction conditions used in these Examples were 300 ppm rhodium and a 14:1 Ligand A to rhodium ratio.

EXAMPLE XXXIV

Butadiene Hydroformylation in THF/Ethylene Glycol, Pyridinium Tosylate

A catalyst solution including 8.2 mg pyridinium tosylate (1 mole/mole rhodium) was prepared in 22 mL THF, 4 mL ethylene glycol (2 mol diol/mole butadiene) and charged to a 100 mL Parr reactor. Butadiene (3 mL) was added to the reactor as a liquid under pressure. The mixture was heated to 110° C. and pressurized to 900 psi with 4:1 CO:H$_2$. The reaction rate was followed by monitoring the syngas uptake. Syngas (1:1 CO:H$_2$) was periodically recharged to the reactor to maintain a constant pressure at 900 psi. The initial reaction rate was found to be 4.8 mol/1-hr. After two hours reaction time the mixture was analyzed by gas chromatography to determine the product composition. The products consisted of 35% C5 aldehyde acetals, 13% diacetals of branched C6 dialdehydes, 36% adipaldehyde acetal, and 17% dialdehyde monoacetals.

EXAMPLE XXXV

Butadiene Hydroformylation in THF/2.3-Butanediol, Pyridinium Tosylate

A catalyst solution including 8.4 mg pyridinium tosylate (1 mole/mole rhodium) was prepared in 13 mL THF, 12 mL 2,3-butanediol (4 mol diol/mole butadiene) and charged to a 100 mL Parr reactor. Butadiene (3 mL) was added to the reactor as a liquid under pressure. The mixture was heated to 95° C. and pressurized to 500 psi with 1:1 CO:H$_2$. The reaction rate was followed by monitoring the syngas uptake. The reaction rate was found to be 2.5 mol/1-hr. After two hours reaction time the mixture was analyzed by gas chromatography to determine the product composition. All the oxo products were converted to acetals, and consisted of 33% C5 aldehyde acetals, 8% diacetals of branched C6 dialdehydes, and 57% adipaldehyde acetal.

EXAMPLE XXXVI

Butadiene Hydroformylation in THF/2.3-Butanediol Pyridinium Tosylate

A catalyst solution including 8.2 mg pyridinium tosylate (1 mole/mole rhodium) was prepared in 19 mL THF, 6 mL 2,3-butanediol (2 mol diol/mole butadiene) and charged to a 100 mL Parr reactor. Butadiene (3 mL) was added to the reactor as a liquid under pressure. The mixture was heated to 110° C. and pressurized to 900 psi with 4:1 CO:H$_2$. The reaction rate was followed by monitoring the syngas uptake. Syngas (1:1 CO:H$_2$) was periodically recharged to the reactor to maintain a constant pressure at 900 psi. The initial reaction rate was found to be 8.1 mol/1-hr. After two hours reaction time the mixture was analyzed by gas chromatography to determine the product composition. The oxo products were all converted to acetals and consisted of 35% C5 aldehyde acetals, 14% diacetals of branched C6 dialdehydes, and 47% adipaldehyde acetal.

EXAMPLE XXXVII

This Example illustrates the hydroformylation of butadiene under conditions favoring the formation of a 3-pentenal intermediate (i.e., high partial pressure of CO), the removal of the 3-pentenal, formation of an acetal of 3-pentenal and further hydroformylation of the acetal to adipaldehyde monoacetal.

(A) A catalyst solution consisting of 0.016 g Rh(CO)$_2$acac and 2.089 g Ligand A (3.6 Ligand A to rhodium ratio) and 160 mL tetraglyme solvent was charged to a 300 mL Parr autoclave. Butadiene (35 mL) was charged as a liquid under pressure. The reaction was heated to 95° C. and pressurized to 900 psi with 4:1 CO:H$_2$. The reaction was periodically repressurized to 900 psi with 1:1 syngas to compensate for that absorbed by the solution. After 2.5 hours, the reactor was cooled and recharged with 35 mL butadiene and the reaction repeated. A total of three 35 -mL butadiene charges were reacted in order to provide enough material for distillation. The mixture was analyzed by gas chromatography to determine the product composition. The hydroformylation products consisted of 53% pentenals, 27% valeraldehyde, and 12% adipaldehyde.

(B) The product mixture was distilled at 260 mm Hg through a 25-tray Oldershaw column. The best distillation cuts were collected at a kettle temperature of 225° and consisted of a solution containing 77% pentenals.

(C) A round-bottom flask was charged with 5.2 g of the solution produced in step (B) above (approximately 0.06 mol pentenals), 4.99 g 2,3-butanediol (1 mole/mole pentenals), 75 mL benzene and 1.53 g pyridinium tosylate. This mixture was stirred at 25° C. for 16 hours, then heated to 60° C. for 1 hour to complete the reaction. A small amount of unreacted butanediol remained in the mixture 0.2 g of the pentenal solution was added and the mixture stirred for an additional hour at 60° C. until the butanediol could not be detected by gas chromatography of the solution.

(D) A 100 mL Parr reactor was charged with 0.019 g Rh(CO)$_2$acac, 0.88 g Ligand A (14.1 Ligand A to rhodium ratio), 15 mL benzene and 10 mL of the pentenal acetal solution produced in step (C) above. This mixture was heated to 85° and pressurized to 500 psig with syngas (1:1 CO:H$_2$). The syngas was periodically recharged to maintain a constant pressure of 500 psig in the reactor. After 4 hours, the mixture was analyzed by gas chromatography. The pentenal acetals were 80% converted to dialdehyde monoacetals, with an N:I ratio of 3.5, corresponding to 79% adipaldehyde monoacetal.

(E) The adipaldehyde monoacetal product of step (D) above can be readily converted to adipaldehyde by hydrolysis with an acid catalyst.

EXAMPLE XXXVIII

This Example illustrates the hydroformylation of isoprene with Rh/Ligand A catalyst. A catalyst solution consisting of 0.019 g Rh(CO)$_2$(acac)(300 ppm rhodium), 0.89 g Ligand A (14:1 ligand to rhodium ratio) and 25 mL tetrahydrofuran was charged to a 100 mL Parr reactor. Isoprene (3 mL) was charged to the reactor as a liquid under pressure. The reaction was heated to 95° C. and pressurized to 500 psig with 1:1 CO:H$_2$. The reaction rate was determined by monitoring the rate of syngas consumption. The rate of reaction was found to be 1.7 mol/l-hr. Syngas was periodically recharged to maintain a constant pressure of 500 psig. After two hours of reaction the solution was analyzed by gas chromatography to determine product composition. The isoprene had been 89% converted. The products consisted of 20% 2-methyl-4-pentenal, 27% 4-methyl-4-pentenal, 9% branched methylhexanedials and 33% 2-methyl-hexane-1,6-dial.

Comparative Examples XXXIX and XL below illustrate that the hydroformylation of butadiene with Rh/triphenylphosphine or Rh/bis(diphenyl-phosphino)propane catalysts under the conditions used in Example I above give only C$_5$ aldehydes with no adipaldehyde.

EXAMPLE XXXIX (COMPARATIVE)

Hydroformylation of Butadiene with Triphenylphosphine/Rhodium Catalyst

A catalyst solution consisting of 0.019 g Rh(CO)$_2$.(acac) (300 ppm rhodium), 0.29 g triphenylphophine ligand (15:1 ligand to rhodium ratio) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 CO:H$_2$. After two hours of reaction the solution was analyzed by gas chromatography to determine product composition. Butadiene was approximately 30% converted. The products consisted of only C$_5$ aldehydes, with no dialdehyde present.

EXAMPLE XL (COMPARATIVE)

Hydroformylation of Butadiene with Bis(diphenylphosphino)propane/Rhodium Catalyst.

A catalyst solution consisting of 0.019 g Rh(CO)$_2$.(acac) (300 ppm rhodium), 0.24 g bis(diphenyl-phosphino)propane ligand (8:1 ligand to rhodium ratio) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 CO:H$_2$. After two hours of reaction the solution was analyzed by gas chromatography to determine product composition. Butadiene was 50% converted. The products consisted of only C$_5$ aldehydes, with no dialdehyde present.

EXAMPLE XLI

Butadiene Hydroformylation in THF/Methanol

This Example illustrates that the hydroformylation of butadiene in the presence of methanol produces less conversion to acetals than observed in the presence of 1,2-, 1,3- or 2,4-diols. The reaction was run with 300 ppm rhodium, Ligand A/rhodium=14. A catalyst solution was prepared in 15 mL THF, 10.8 mL ethylene glycol (7 mol diol/mole butadiene), and charged to a 100 mL Parr reactor. Butadiene (3 mL) was added to the reactor as a liquid under pressure. The mixture was heated to 95° C. and pressurized to 500 psi with 1:1 CO:H$_2$. The reaction rate was followed by monitoring the syngas uptake. Syngas (1:1 CO:H$_2$) was periodically recharged to the reactor to maintain a constant pressure at 500 psi. The initial reaction rate was found to be 4.5 mol/l-hr. After two hours reaction time the mixture was analyzed by gas chromatography to determine the product composition. Butadiene was 92% converted. The products consisted of 63% C$_5$ aldehydes, 37% C$_5$ aldehyde acetals, with no formation of dialdehydes or dialdehyde acetals.

Examples XLII to XLVI below illustrate the hydroformylation of butadiene with several Rh/bis- phosphite catalysts outside the scope of Formula (I) above to give low butadiene conversion, with no dialdehydes produced. Aside from the ligand, the conditions used were similar to the conditions used in Example I above.

EXAMPLE XLIII (COMPARATIVE)

Hydroformylation of Butadiene with (isoBHA-P)(binaphthyl-P)(isoBHA-diol)/Rhodium Catalyst (Ligand G)

A catalyst solution consisting of 0.019 g $Rh(CO)_2$(acac) (300 ppm rhodium), 0.89 g Ligand G (10-15:1 Ligand G to rhodium ratio), 2.19 g N-methylpyrrolidone (as an internal standard) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was 33% converted. The products consisted of 4% valeraldehyde, 96% pentenals, with no dialdehydes present. Ligand G gives good conversions under the conditions of Example LVI below.

EXAMPLE XLIV (COMPARATIVE)

Hydroformylation of Butadiene with (isoBHA-P)$_2$(1,4-butanediol)/Rhodium Catalyst (Ligand I)

A catalyst solution consisting of 0.019 g $Rh(CO)_2$(acac) (300 ppm rhodium), 0.88 g Ligand I (10-15:1 Ligand I to rhodium ratio), 2.52 g N-methylpyrrolidone (as an internal standard) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was less than 5% converted.

EXAMPLE XLV (COMPARATIVE)

Hydroformylation of Butadiene with (isoBHA-P)$_2$(2,2-dimethyl-1,3-propanediol)/Rhodium Catalyst (Ligand J)

A catalyst solution consisting of 0.019 g $Rh(CO)_2$(acac) (300 ppm rhodium), 0.88 g Ligand J (10-15:1 Ligand J to rhodium ratio), 2.19 g N-methylpyrrolidone (as an internal standard) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was 33% converted. The products consisted of 8% valeraldehyde, 92% pentenals, with no dialdehydes present.

EXAMPLE XLVI (COMPARATIVE)

Hydroformylation of Butadiene with (Biphenol-P)$_2$(HO-($C_6H_3$-tB7)-$O_2$C-C($C_2H_5$)$_2$-$CO_2$-($C_6H_3$-tBu)-OH)/Rhodium Catalyst (Ligand K)

A catalyst solution consisting of 0.019 g $Rh(CO)_2$(acac) (300 ppm rhodium), 0.88 g Ligand K (10-15:1 Ligand K to rhodium ratio), 2.40 g N-methylpyrrolidone (as an internal standard) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was 71% converted. The products consisted of 6% valeraldehyde, 94% pentenals, with no dialdehydes present.

EXAMPLE XLVII (COMPARATIVE)

Hydroformylation of Butadiene with Ligand L/Rhodium Catalyst

A catalyst solution consisting of 0.019 g $Rh(CO)_2$(acac) (300 ppm rhodium), 0.86 g Ligand L (22:1 Ligand L to rhodium ratio) and 25 mL tetrahydrofuran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was less than 5% converted.

The results of several of the above Examples are tabulated in Table III.

TABLE III

| Example | Ligand | Butadiene Conversion | Rate | Valeraldehyde | Adipaldehyde |
|---|---|---|---|---|---|
| I | A | 92% | 1.7 | 61% | 26% |
| XXVI | B | 95% | 0.4 | 7% | 10% |
| XXVII* | C | 68% | 1.2 | 8% | 5% |
| XLIII* | G | 33% | — | 4% | 0% |
| XLIV* | I | <5% | | | |
| XLVI* | K | <5% | | | |
| XLV* | J | 33% | | 8% | 0% |

*Comparative Example (Note that Ligand C gives good conversions under the conditions of Example LV below and Ligand G gives good conversions under the conditions of Example LVI below.)

Under the conditions of Example I above, triphenylphosphite and Ligand L were completely unreactive even at 100° C. and 1000 psi syngas. Under similar conditions, the non-basic phosphine $P(CH_2CH_2CN)_3$ produced mostly branched dialdehyde (i.e., 4-methyl pentanedial).

EXAMPLE XLVIII

Synthesis and hydroformylation of the 2,4-pentanediol acetal of 3-pentenal

A. A round-bottom flask was charged with 6.6 g of a 3-pentenal solution prepared as in Example XXXVII (approximately 0.08 mol pentenals), 10.03 g 2,4-pentanediol (1 mole/mole pentenals), 100 mL toluene and 3.16 g pyridinium tosylate. The mixture was stirred at 25° C. for 16 hours, then heated at 70° C. for 2 hours to complete the reaction. The solution was extracted with three 100 mL-portions of water to remove any unreacted diol, then dried by refluxing and collecting water in a Dean-Stark trap. The products consisted of 8.6% valeraldehyde acetal, 63.0% pentenal acetals, and 28.4% heavy products resulting from Michael addition of the 2,4-pentanediol across the double bond of the pentenal acetals.

B. A 100 mL Parr reactor was charged with 0.019 g $Rh(CO)_2$acac, 0.49 g Ligand A (8:1 Ligand A to rhodium ratio), 12 mL toluene and 13 mL of the 3-pentenal acetal solution produced in A above. The mixture was heated to 110° and pressurized to 500 psig with 1:1 $CO:H_2$. The syngas was periodically recharged to maintain a constant pressure of 500 psig. After 3 hours, the mixture was analyzed by gas chromatography. 84% of the pentenal acetals had been converted to dialdehyde monoacetals, consisting of 15.9% branched dialdehyde acetals and 84.5% adipaldehyde monoacetal.

EXAMPLE XLIX

SYNTHESIS AND HYDROFORMYLATION OF THE PINACOL ACETAL OF 3-PENTENAL

A. A round-bottom flask was charged with 15.4 g of a pentenal solution prepared as in Example XXXVII above (approximately 0.18 mol pentenals), 21.7 g pinacol (1 mole/mole pentenals), 95 mL toluene, and 12.78 g pyridinium tosylate. The flask was fitted with a reflux condenser and Dean-Stark trap for water removal. The mixture was heated to reflux for 1 hour. Gas chromatographic analysis showed complete conversion of the pentenals. The solution was extracted with three 100 mL-portions of water to remove any unreacted diol, then dried by refluxing 30 minutes and collecting water in a Dean-Stark trap. The products consisted of 8.2% valeraldehyde acetal, 73.4% pentenal acetals and 18.5% heavy products resulting from Michael addition of pinacol across the double bond of the pentenal acetals.

B. A 100 mL Parr reactor was charged with 0.019 g $Rh(CO)_2acac$, 0.49 g Ligand A (8:1 Ligand A to rhodium ratio), 12 mL toluene, and 10 mL of the 3-pentenal acetal solution. The mixture was heated to 110° and pressurized to 500 psig with 1:2 $CO:H_2$. The syngas was periodically recharged to maintain a constant pressure of 500 psig. After 2 hours, the mixture was analyzed by gas chromatography. The pentenal acetals were 100% converted to dialdehyde monoacetals, consisting of 14.9% branched dialdehyde mono-acetals and 81.3% adipaldehyde monoacetal.

EXAMPLE L (COMPARATIVE)

Theoretically, the adverse affects of water and phosphorous acid on the process of this invention might be circumvented with additives. This theory was tested using the reaction conditions set out in Example I above. Triethyl orthoformate and molecular sieves were added to the reaction mixture to absorb water generated in the acetal synthesis. Cyclohexene oxide and a cycloaliphatic epoxide were added to the reaction mixture to scavenge phosphorous acids before they could catalyze Ligand A decomposition. In all cases, when one of these additives was used, no acetal formation took place and the primary reaction product was valeraldehyde. The adverse effects of water and phosphorous acids are successfully avoided by the preferred embodiment of this invention illustrated by Example XXXVII above.

EXAMPLE LI (COMPARATIVE)

A. Several additives (e.g., olefin isomerization catalysts such as $PdCl_2$ that might assist the isomerization of 3-pentenal to 4-pentenal to increase the second hydroformylation to adipaldehyde) were introduced into the reaction mixtures used in Example I above in attempts to improve the selectivity of 1,6-hexanedial. However, there was no effect.

B. In addition, "co-metals" (cobalt and ruthenium) were added to the reaction mixture of Example I above (usually in a 1:1 ratio with rhodium) and mostly valeraldehyde was produced. $Ru_3(CO)_{12}$ alone and modified with Ligand A did not hydroformylate butadiene at 95° and 500 psi syngas.

C. Lewis acids (triphenylboron and aluminum chloride) were also added to the reaction mixture used in Example I because they have been shown to improve selectivity to linear dinitrile in the nickel-catalyzed hydrocyanation of butadiene to adiponitrile. However, even a large excess of Lewis acid over rhodium had no effect on selectivity. Addition of an anion promoter (i.e., tetrabutylphosphonium acetate resulted in a slower reaction than normal, producing mostly pentenals over the 2-hour period, although small amounts of adipaldehyde were produced.

Examples LII and LIII below illustrate the cohydroformylation of butadiene and an a-mono-olefin in accordance with the process of the present invention.

EXAMPLE LII

Butadiene/Ethylene Hydroformylation

A catalyst solution consisting of 0.019 g $Rh(CO)_2$(acac) (300 ppm rhodium), 0.88 g Ligand A (14:1 Ligand A to rhodium ratio), 2.6 g N-methyl-pyrrolidone (as an internal standard), and 25 mL tetrahydrofuran was charged to a 100 mL Parr reactor. Butadiene (3 mL) was charged to the reactor as a liquid under pressure. The reaction was pressurized to 100 psi with ethylene, heated to 95° C., and then 1:1 $CO:H_2$ was added to a total pressure of 600 psi. The reaction rate for ethylene and butadiene was determined by monitoring the formation of propionaldehyde and butadiene hydroformylation products by gas chromatography. After 10 minutes of reaction, ethylene was found to be reacting at a rate of 2.9 mol/1-hr. After one hour, the rate of ethylene hydroformylation had decreased to 1.6 mol/1-hr. Butadiene hydroformylation proceeded at a rate of 0.7 mol/1-hr. After two hours of reaction the solution was analyzed by gas chromatography to determine product composition. Butadiene was 99% converted. The oxo products consisted of 2.6 g valeraldehyde, 0.1 g pentenals, 0.3 g branched dialdehyde, 0.8 g adipaldehyde, and 2.9 g propionaldehyde.

EXAMPLE LIII

Butadiene/1-Hexene Hydroformylation

A catalyst solution consisting of 0.019 g $Rh(CO)_2$(acac) (300 ppm rhodium), 0.99 g Ligand A (14:1 Ligand A to rhodium ratio), 2.2 g N-methylpyrrolidone (as an internal standard), 2 mL 1-hexene, and 25 mL tetrahydrofuran was charged to a 100 mL Parr reactor. Butadiene (2 mL) was charged to the reactor as a liquid under pressure. The reaction was pressurized to 500 psi with 1:1 $CO:H_2$. The reaction rate for 1-hexene and butadiene was determined by monitoring 1-hexene conversion and the formation of butadiene hydroformylation products by gas chromatography. After 20 minutes of reaction, 1-hexene was found to be 84% converted, corresponding to a rate of 1.39 mol/1-hr. Butadiene hydroformylation proceeded at a rate of 1.0 mol/1-hr. After two hours of reaction the solution was analyzed by gas chromatography to determine product composition. Butadiene was 96% converted. The oxo products consisted of 0.7 g valeraldehyde, 0.1 g pentenals, 0.1 g branched dialdehyde, 0.2 g adipaldehyde, and 1.8 g heptanal.

EXAMPLE LIV

Butadiene Hydroformylation to Pentenals, Larger Butadiene Charge

This example illustrates that, when pentenals are synthesized by initially charging larger amounts of butadiene, greater efficiency to pentenals is obtained as compared with Example XXXVII above in which butadiene was charged in three 35-mL portions).

A catalyst solution consisting of 0.136 g Rh(CO₂acac and 3.00 g Ligand A (3.6:1 Ligand A rhodium ratio on mole basis) and 150 mL tetrahydrofuran solvent was charged to a 300 mL Parr autoclave. Butadiene (100 mL) was charged as a liquid under pressure. The reaction was heated to 95° C. and pressurized to 800 psi with 4:1 $CO:H_2$. The reaction was periodically repressurized to 900 psi with 1:1 syngas to compensate for that absorbed by the solution. After 4 hours, the mixture was analyzed by gas chromatography to determine the product composition. The hydroformylation products consisted of 80% pentenals, 11% valeraldehyde, and 4% adipaldehyde.

EXAMPLE LV

Butadiene Hydroformylation in THF/Ethylene Glycol

A catalyst solution consisting of 0.019 g Rh(CO)₂acac and 0.88 g Ligand C (14:1 Ligand C/rhodium ratio) was prepared in 13 mL THF, 12 mL ethylene glycol (7 mol diol/mole butadiene), and charged to a 100 mL Parr reactor. Butadiene (3 mL) was added to the reactor as a liquid under pressure. The mixture was heated to 110° C. and pressurized to 900 psi with 4:1 $CO:H_2$. After two hours reaction time the mixture was analyzed by gas chromatography to determine the product composition. Butadiene was 98% converted. The products consisted of 51% C₅ aldehyde acetals, 11% diacetals of branched C₆ dialdehydes, and 37% adipaldehyde acetal.

EXAMPLE LVI

Butadiene Hydroformylation in THF/Ethylene Glycol Rh/(isoBHA-P)(Binaphthyl-P)(isoBHA diol) [Ligand G] Catalyst A catalyst solution consisting of 0.019 g Rh(CO)₂acac and 8.8 g Ligand G (10–15 moles Ligand per mole Rh) was prepared in 13 mL THF, 12 mL ethylene glycol (7 mol diol/mole butadiene), and charged to a 100 mL Parr reactor. Butadiene (3 mL) was added to the reactor as a liquid under pressure. The mixture was heated to 110° C. and pressurized to 900 psi with 4:1 $CO:H_2$. After two hours reaction time the mixture was analyzed by gas chromatography to determine the product composition. Butadiene was 74% converted. The products consisted of 48% C₅ aldehyde acetals, 23% diacetals of branched C₆ dialdehydes and 28% adipaldehyde acetals.

Examples LVII to LXII below illustrate the poorer results (i.e., low butadiene conversions and/or low adipaldehyde selectivity) generally obtained using ligands outside the scope of Formula (I) above.

EXAMPLE LVII (COMPARATIVE)

Hydroformylation of Butadiene with Ligand D/Rhodium Catalyst

A catalyst solution consisting of 0.019 g Rh(CO)₂-(acac)(300 ppm rhodium), 0.36 g Ligand D (8:1 Ligand D to rhodium ratio), and 25 mL tetrahydrofuran was charged to a 100 mL Parr reactor. Butadiene (3 mL) was charged to the reactor as a liquid under pressure. The reaction was heated to 96° C. and pressurized to 500 psig with 1:1 CO:H. After two hours of reaction the solution was analyzed by gas chromatography to determine product composition. No hydroformylation of butadiene was observed under these conditions.

EXAMPLE LVIII (COMPARATIVE)

Hydroformylation of Butadiene with Ligand E/Rhodium Catalyst

A catalyst solution consisting of 0.019 g Rh(CO)₂-(acac)(300 ppm rhodium), 0.50 g Ligand E (8:1 Ligand E to rhodium ratio), and 25 mL tetrahydroruran was charged to a 100 mL parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. No hydroformylation of butadiene was observed under the conditions.

EXAMPLE LIX (COMPARATIVE)

Hydroformylation of Butadiene with Ligand F/Rhodium Catalyst

A catalyst solution consisting of 0.019 g Rh(CO)₂-(acac)(300 ppm rhodium), 0.42 g Ligand F (6:1 Ligand F to rhodium ratio), and 2.32 g N-methylpyrrolidone (as an internal standard) and 25 mL tetrahydroruran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was 65% converted. The products consisted only of pentenals.

EXAMPLE LX (COMPARATIVE)

Hydroformylation of Butadiene with Ligand F/Rhodium Catalyst

A catalyst solution consisting of 0.019 g Rh(CO)₂-(acac)(300 ppm rhodium), 0.42 g Ligand F (6:1 Ligand F to rhodium ratio), and 2.32 g N-methylpyrrolidone (as an internal standard) and 25 mL tetrahydroruran was charged to a 100 mL Parr reactor. Butadiene (3 mL) was charged to the reactor as a liquid under pressure. The reaction was heated to 110° C. and pressurized to 1000 psig with 1:1 $CO:H_2$. After two hours of reaction the solution was analyzed by gas chromatography to determine product composition. Butadiene was 65% converted. The products consisted of 53% valeraldehyde, 14% pentenals, 29% branched dialdehydes, and only 4% adipaldehyde.

EXAMPLE LXI (COMPARATIVE)

Hydroformylation of Butadiene with Ligand H/Rhodium Catalyst

A catalyst solution consisting of 0.019 g Rh(CO)₂-(acac)(300 ppm rhodium), 0.13 g Ligand H to rhodium ratio), and 2.35 g N-methylpyrrolidone (as an internal standard) and 25 mL tetrahydroruran was charged to a 100 mL Parr reactor. Butadiene (3 mL) was charged to the reactor as a liquid under pressure. The reaction was heated to 95° C. and pressurized to 500 psig with 1:1 $CO:H_2$. After two hours of reaction the solution was analyzed by gas chromatography to determine product composition. Butadiene was 63% converted. The products consisted of 6% valeraldehyde, 94% pentenals.

EXAMPLE LXII (COMPARATIVE)

Hydroformylation of Butadiene with Ligand H/Rhodium Catalyst

A catalyst solution consisting of 0.019 g $Rh(CO)_2$-(acac)(300 ppm rhodium), 0.13 g Ligand H (2:1 Ligand H to rhodium ratio), and 2.35 g N-methylpyrrolidone (as an internal standard) and 25 mL tetrahydroruran was charged to a 100 mL Parr reactor. Butadiene (3 mL) was charged to the reactor as a liquid under pressure. The reaction was heated to 110° C. and pressurized to 1000 psig with 1:1 $CO:H_2$. After two hours of reaction the solution was analyzed by gas chromatography to determine product composition. Butadiene was 100% converted. The products consisted of 38% valeraldehyde, 15% 2-methylbutanal, 39% branched dialdehydes, and 7% adipaldehyde.

EXAMPLE LXIII

Hydroformylation of Dimethylbutadiene with Ligand A/Rhodium Catalyst

A catalyst solution consisting of 0.019 g $Rh(CO)_2$-(acac) (300 ppm rhodium), 0.49 g Ligand A(8:1 Ligand A to rhodium ratio) and 25 mL tetrahydrofuran was charged to a 100 mL Parr reactor. Dimethylbutadine (3 mL) was charged to the reactor as a liquid. The reaction was heated to 110° C. and pressurized to 1000 psig with 1:1 $CO:H_2$. After four hours of reaction the solution was analyzed by gas chromatography to determine product composition. (Conversion could not be determined since dimethylbutadiene co-euluted with the solvent peak.) The product selectivities consisted of 22% 3,4-dimethyl-4-penten-1-al, 5% 3,4-dimethylpentanal, 43% 3,4-dimethyl-2-penten-1-al and 28% 3,4-dimethyl-6-hexanedial.

EXAMPLE LXIV (COMPARATIVE)

Hydroformylation of 1,3-Pentadiene (piperylene) with Ligand A/Rhodium catalyst

A catalyst solution consisting of 0.019 g $Rh(CO)_2$-(acac) (300 ppm rhodium), 0.49 g Ligand A (8:1 Ligand A to rhodium ratio) and 25 Ml tetrahydrofuran was charged to a 100 mL Parr reactor. Piperylene (3 ML) was charged to the reactor as a liquid. The reaction was heated to 100° C. and pressurized to 1000 psig with 1:1 $CO:H_2$. After two hours of reaction the solution was analyzed by gas chromatography to determine product composition. Piperylene was 98% converted. The product selectivites consisted of 14% 2-methylvaleraldehyde, 20% hexanal, 35% hexenals, 22% branched dialdehydes and 8% 1,7-heptanedial.

EXAMPLE LXV

Butadiene Hydroformylation with Ligand M/Rhodium Catalyst

A catalyst solution consisting of 0.019 g $Rh(CO)_2$-(acac) (300 ppm rhodium), 0.11 g Ligand M (2:1 ligand to rhodium ratio) and 2.5 mL tetrahydrofuran was charged to a 100 mL Parr reactor. Butadiene (3 mL) was charged to the reactor as a liquid under pressure. The reaction was heated to 115° C. and pressurized to 1000 psig with 1:1 $CH:H_2$) consumption. The rate of reaction was found to be 2.5 mol/1-hr. After two hours of reaction the solution was analyzed by gas chromatography to determine the product composition. The products consisted of 68% valeraldehyde, 7% branched dialdehyde, and 21% adipaldehyde.

EXAMPLE LXVI

Butadiene Hydroformylation with Ligand N/Rhodium Catalyst

A catalyst solution consisting of 0.019 g $Rh(CO)_2$-(acac) (300 ppm rhodium), 0.11 g Ligand N (2:1 ligand to rhodium ratio) and 2.5 mL tetrahydrofuran was charged to a 100 mL Parr reactor. Butadiene (3 mL) was charged to the reactor as a liquid under pressure. The reaction was heated to 115° C. and pressurized to 1000 psig with 1:1 $CO:H_2$. After two hours of reaction the solution was analyzed by gas chromatography to determine the product composition. The products consisted of 68% valeraldehyde, 10% branched dialdehyde, and 22% adipaldehyde.

EXAMPLE LXVII

Butadiene Hydroformylation with Ligand O/Rhodium Catalyst

A catalyst solution consisting of 0.019 g $Rh(CO)_2$-(acac) (300 ppm rhodium), 0.51 g Ligand O (8:1 ligand to rhodium ratio) and 2.5 mL tetrahydrofuran was charged to a 100 mL Parr reactor. Butadiene (3 mL) was charged to the reactor as a liquid under pressure. The reaction was heated to 95° C. and pressurized to 500 psig with 1:1 $CO:H_2$. The reaction rate was determined by monitoring the rate of syngas (CO and $H_2$) consumption. The rate of reaction was found to be 1.8 mol/1-hr. After two hours of reaction the solution was analyzed by gas chromatography to determine the product composition. The products consisted of 47% valeraldehyde, 8% pentenals. 14% branched dialdehyde, and 18% adipaldehyde.

EXAMPLE LXVIII

Butadiene Hydroformylation with Ligand P/Rhodium Catalyst

A catalyst solution consisting of 0.019 g $Rh(CO)_2$-(acac) (300 ppm rhodium), 0.26 g Ligand P(4:1 ligand to rhodium ratio) and 2.5 mL tetrahydrofuran was charged to a 100 mL Parr reactor. Butadiene (3 mL) was charged to the reactor as a liquid under pressure. The hours of reaction the solution was analyzed by gas chromatography to determine the product composition. The products consisted of 56% valeraldehyde, 2% pentenals, 14% branched dialdehyde, and 27% adipaldehyde.

EXAMPLE LXIX

Butadiene Hydroformylation with Ligand Q/Rhodium Catalyst

A catalyst solution consisting of 0.019 g $Rh(CO)_2$-(acac) (300 ppm rhodium), 0.12 g Ligand Q (2:1 ligand to rhodium ratio) and 25 mL tetrahydrofuran was charged to a 100 mL Parr reactor. Butadiene (3 mL) was charged to the reactor as a liquid under pressure. The reaction was heated to 115° C. and pressurized to 1000 psig with 1:1 $CO:H_2$. The reaction rate was determined by monitoring the rate of syngas (CO and $H_2$) consumption. The rate of reaction was found to be 2.5 mol/1-hr. After two hours of reaction the solution was analyzed by gas chromatography to determine the product composition. The products consisted of 63% valeraldehyde, 9.2% pentenals 7% branched dialdehyde, and 21% adipaldehyde.

EXAMPLE LXX (COMPARATIVE)

Butadiene Hydroformylation with Ligand R/Rhodium Catalyst

A catalyst solution consisting of 0.019 g Rh(CO)$_2$-(acac) (300 ppm rhodium), 0.22 g Ligand R (2:1 ligand to rhodium ratio) and 25 mL tetrahydrofuran was charged to a 100 mL Parr reactor. Butadiene (3 mL) was charged to the reactor as a liquid under pressure. The reaction was heated to 110° C. and pressurized to 1000 psig with 1:1 CO:H$_2$. After 90 minutes of reaction the solution was analyzed by gas chromatography to determine the product composition. Butadiene was 79% converted. The products consisted of 4% valeraldehyde, 77% pentenals 4% branched dialdehyde, and 7% adipaldehyde.

EXAMPLE LXXI (COMPARATIVE)

Butadiene Hydroformylation with Ligand S/Rhodium Catalyst

A catalyst solution consisting of 0.019 g Rh(CO)$_2$-(acac) (300 ppm rhodium), 0.12 g Ligand M (2:1 ligand to rhodium ratio) and 25 mL tetrahydrofuran was charged to a 100 mL Parr reactor. Butadiene (3 mL) was charged to the reactor as a liquid under pressure. The reaction was heated to 11° C. and pressurized to 1000 psig with 1:1 CO:H$_2$. After 90 minutes of reaction the solution was analyzed by gas chromatography to determine the product composition. Butadiene was 33% converted. The product consisted C5 aldehydes.

EXAMPLE LXXII (COMPARATIVE)

Butadiene Hydroformylation with Ligand T/Rhodium Catalyst

A catalyst solution consisting of 0.019 g Rh(CO)$_2$-(acac) (300 ppm rhodium), 0.26 g Ligand T (4:1 ligand to rhodium ratio) and 25 mL tetrahydrofuran was charged to a 100 mL Parr reactor. Butadiene (3 mL) was charged to the reactor as a liquid under pressure. After two hours of reaction the solution was analyzed by gas chromatography to determine the product composition. The products consisted of 13% valeraldehyde, 60% pentenals, 2% branched dialdehyde, and 8% adipaldehyde.

EXAMPLE LXXIII (COMPARATIVE)

Butadiene Hydroformylation with Ligand U/Rhodium Catalyst

A catalyst solution consisting of 0.019 g Rh(CO)2-(acac) (300 ppm rhodium), 8 moles ligand U per mole rhodium, and 25 mL tetrahydrofuran was charged to a 100 mL Parr reactor. Butadiene (3 mL) was charged to the reactor as a liquid under pressure. The reaction was heated to 100° C. and pressurized to 1000 psig with 1:1 CO:H$_2$. After four hours of reaction the butadiene was determined to be 66% converted to C5 aldehydes.

What is claimed is:

1. A hydroformylation process for producing a 1,6-hexanedial which comprises reacting a butadiene with hydrogen and carbon monoxide in the presence of a catalytic amount of rhodium complexed with a polyphosphite ligand having the formula:

$$\left[ Y \begin{matrix} O \\ O \end{matrix} P-O \right]_m [X]$$ (I)

wherein Y is a divalent organic radical that contains at least 5 carbon atoms, X is an organic radical that contains at least 12 carbon atoms, that contains at least two branched alkyl groups and that has a valence of m supplied by carbon atoms of the X radical, provided that at least two of the carbon atoms supplying the valences of the X radical are separated from each other by no more than 10 atoms and m has a value from 2 to 6 inclusive.

2. A process as claimed in claim 1 wherein the the butadiene is butadiene and the 1,6-hexanedial is adipaldehyde.

3. A process as claimed in claim 1 wherein the butadiene is isoprene and the 1,6-hexanedial is 2-methyl-hexane-1,6-dial.

4. A process as claimed in claim 1 wherein the butadiene is dimethylbutadiene and the 1,6-hexanedial is 3,4-dimethyl-1,6-hexanedial.

5. A process as in claim 1 wherein the ligand is represented by the formula:

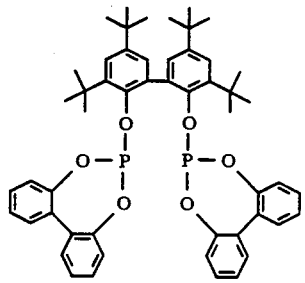

6. A process as in claim 1 wherein the ligand is represented by the formula:

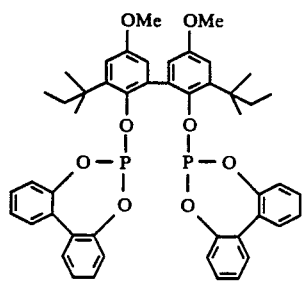

7. A process as in claim 1 wherein the ligand is represented by the formula:

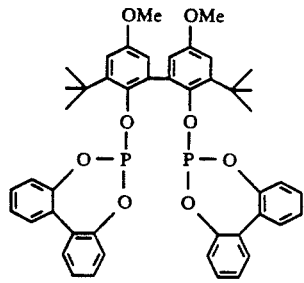

8. A process as in claim 1 wherein the ligand is represented by the formula:

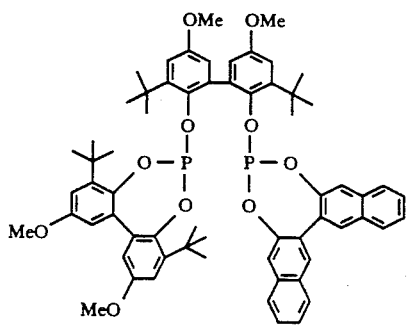

9. A process as claimed in claim 1 wherein the reaction is conducted in the presence of an a-mono-olefin and an aldehyde of the a-mono-olefin is also produced.

10. A process as claimed in claim 1 wherein the ligand has the formula:

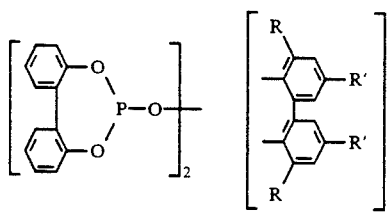

wherein R is a branched alkyl group and R' is a branched alkyl group or an alkoxy group.

11. A hydroformylation process as claimed in claim 1 for producing a 1,6-hexanedial which comprises the steps of:

(A) reacting a butadiene with hydrogen and carbon monoxide in the presence of a catalytic amount of rhodium complexed with a poly-phosphite ligand as claimed in claim 1 to produce a 3-pentenal;

(B) separating the 3-pentenal from the rhodium catalyst before any substantial amount of a, β-pentenal has formed;

(C) reacting the 3-pentenal with a 1,2-diol, a 1,3-diol or a 2,4 diol to produce an acetal of the 3-pentenal and water;

(D) reacting the acetal with hydrogen and carbon monoxide in the presence of a catalytic amount of rhodium complexed with a ligand as claimed in claim 1 to produce a mono-acetal of the 1,6-hexanedial; and (E) converting the monoacetal to the 1,6-hexanedial.

12. A process as claimed in claim 7 where the water formed in step (C) is separated from the 3-pentenal prior to the reaction of the 3-pentenal in step (D).

13. A process as claimed in claim 1 wherein the Ligand has the formula:

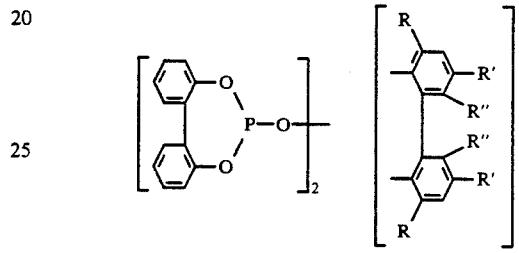

wherein R is a branched alkyl group, R' is hydrogen, an alkyl group or an alkoxy group and R" is hydrogen or an alkyl group.

14. A process as claimed in claim 1 wherein the process is conducted at a temperature from about 50° C. to 150° C. and at a total pressure from about 200 psig to about 1000 psig.

15. A process as claimed in claim 1 wherein:

(i) the butadiene is a conjugated aliphatic olefin having the structure:

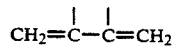

which is linear or branched and can contain alkyl groups, halogen atoms, amino groups or silyl groups as substituents;

(ii) the divalent organic radical represented by Y in formula (I) is a monocyclic or polycyclic unsubstituted monovalent hydrocarbon radical; and (iii) wherein the organic radical represented by X in formula (I) is a monocyclic or polycyclic divalent hydrocarbon radical having at least two branched alkyl substituents.

16. A process as claimed in claim 9 wherein the mono-olefin is ethylene or hexane and the aldehyde is propionaldehyde or heptanal.

* * * * *